(12) United States Patent
Rosenblatt et al.

(10) Patent No.: US 11,446,137 B2
(45) Date of Patent: Sep. 20, 2022

(54) FLEXIBLE KERATOPROSTHESIS DEVICES AND USES THEREOF

(71) Applicant: THE BOARD OF TRUSTEES OF THE UNIVERSITY OF ILLINOIS, Urbana, IL (US)

(72) Inventors: Mark Rosenblatt, Chicago, IL (US); Charles Yu, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 16/608,263

(22) PCT Filed: Apr. 27, 2018

(86) PCT No.: PCT/US2018/029964
§ 371 (c)(1),
(2) Date: Oct. 25, 2019

(87) PCT Pub. No.: WO2018/201057
PCT Pub. Date: Nov. 1, 2018

(65) Prior Publication Data
US 2020/0261213 A1    Aug. 20, 2020

Related U.S. Application Data

(60) Provisional application No. 62/491,438, filed on Apr. 28, 2017.

(51) Int. Cl.
*A61F 2/14*    (2006.01)
(52) U.S. Cl.
CPC ............... *A61F 2/142* (2013.01); *A61F 2/15* (2015.04)

(58) Field of Classification Search
CPC .... A61F 2/142; A61F 2/15; A61F 2002/1681; A61F 2002/1683; A61F 2002/169;
(Continued)

(56) References Cited

U.S. PATENT DOCUMENTS 4,785,758 A * 11/1988 Eichelberger, Sr. .... B63B 21/46
114/299
6,106,552 A    8/2000 Lacombe et al.
(Continued)

FOREIGN PATENT DOCUMENTS

EP      3122287 A1    2/2017
WO   WO-97/27824 A1   8/1997
(Continued)

OTHER PUBLICATIONS

International Application No. PCT/US2018/029964, International Search Report and Written Opinion, dated Aug. 22, 2018.
(Continued)

*Primary Examiner* — Paul B Prebilic
(74) *Attorney, Agent, or Firm* — Marshall, Gerstein & Borun LLP

(57) ABSTRACT

Described herein are flexible keratoprosthesis devices and uses thereof. The keratoprosthesis devices (100) can include an anchor body (110) and a plurality of flexible haptics (120), wherein the plurality of flexible haptics can be attached to and can be capable of extending radially from the anchor body. The flexible keratoprosthesis devices can be implanted into the eye via a minimally invasive technique.

21 Claims, 20 Drawing Sheets

(58) Field of Classification Search
CPC .. A61F 2002/16901; A61F 2002/16902; A61F 2002/16905; A61F 2002/169051; A61F 2002/169053; A61F 2/1694; A61F 2220/0008; A61F 2220/0025; A61F 2220/0033; A61F 2230/005; A61F 2230/0069; A61F 2250/001; A61F 2250/0029; A61F 2250/0039; A61F 2250/006–2250/0063

See application file for complete search history.

(56) References Cited

U.S. PATENT DOCUMENTS

| | | | |
|---|---|---|---|
| 6,254,637 | B1 | 7/2001 | Lee et al. |
| 2001/0042286 | A1* | 11/2001 | Henriott .............. B60B 33/0042 16/29 |
| 2013/0116781 | A1* | 5/2013 | Ben Nun .................. A61F 2/16 623/6.43 |
| 2015/0223930 | A1 | 8/2015 | Shiuey |
| 2015/0305856 | A1* | 10/2015 | Ichikawa .............. A61F 2/1613 623/6.44 |
| 2016/0220354 | A1* | 8/2016 | Lee ........................ A61F 2/1694 |
| 2017/0296331 | A1* | 10/2017 | Werblin ................ A61F 2/1648 |

FOREIGN PATENT DOCUMENTS

| | | |
|---|---|---|
| WO | WO-2008/150319 A1 | 12/2008 |
| WO | WO-2011/020074 A1 | 2/2011 |
| WO | WO-2018/039478 A1 | 3/2018 |

OTHER PUBLICATIONS

Singapore Patent Application No. 11201910016V, Search Report, dated Nov. 20, 2020.
Singapore Patent Application No. 11201910016V, Written Opinion, dated Nov. 27, 2020.
Indian Patent Application No. 201917043381, Examination Report, dated Jan. 12, 2022.

* cited by examiner

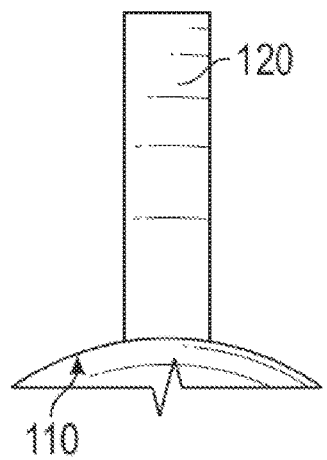 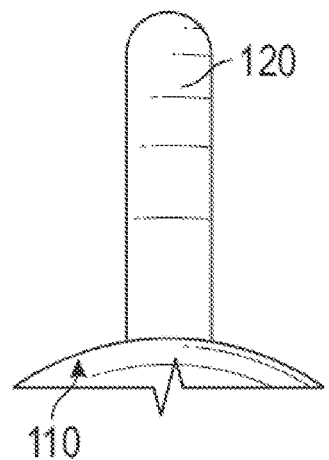 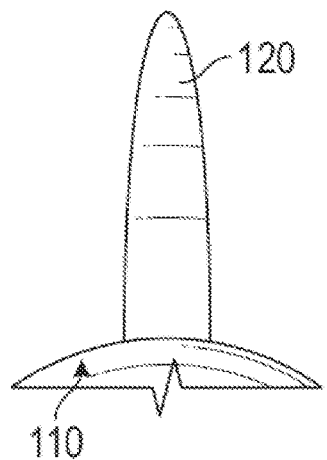
FIG. 3A   FIG. 3B   FIG. 3C
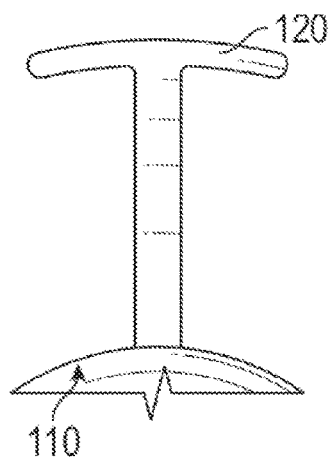 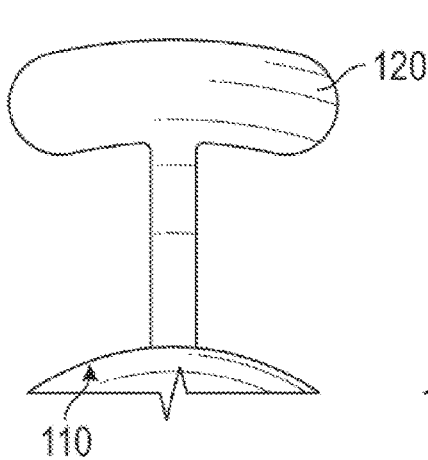 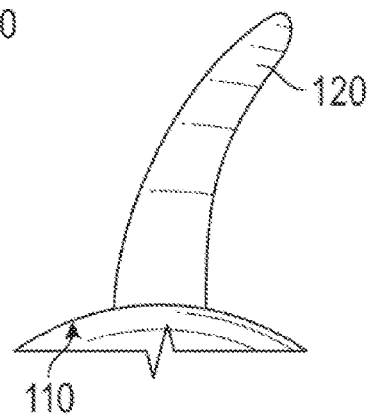
FIG. 3D   FIG. 3E   FIG. 3F
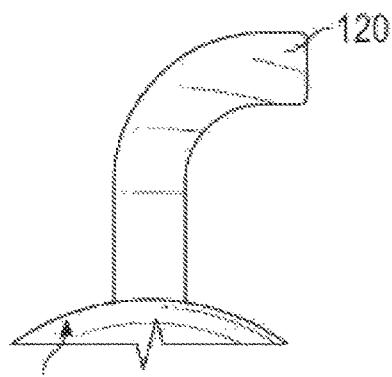
FIG. 3G

FLEXIBLE KERATOPROSTHESIS DEVICES AND USES THEREOF

CROSS-REFERENCE TO RELATED APPLICATIONS

This application is the US national phase of international application PCT/US2018/029964, filed Apr. 27, 2018, which claims the benefit of and priority to U.S. Provisional Patent Application No. 62/491,438, filed on Apr. 28, 2017, entitled "Keratoprosthesis with flexible component for treatment of corneal blindness," the contents of which is incorporated by reference herein in its entirety.

STATEMENT REGARDING FEDERALLY SPONSORED RESEARCH

This invention was made with government support under grant number 5K12EY021475 awarded by the National Institutes of Health. The government has certain rights in the invention.

BACKGROUND

Keratoprosthesis implantation is a procedure that involves full-thickness removal of the cornea and replacement with an artificial cornea. The need for keratoprosthesis implantation arises from failed cornea transplants, unsuitable candidacy for cornea transplants, and a shortage of donor corneas. As such there exists a need for the development of keratoprosthesis devices.

SUMMARY

Described herein are aspects of a keratoprosthesis (Kpro) device that can include an anchor body; and a plurality of flexible haptics, wherein the plurality of flexible haptics can be attached to and can be capable of extending radially from the anchor body. The Kpro device can further include a front plate, wherein the front plate can be attached to the anchor body such that the Kpro device is a single implantable device.

In some aspects the anchor body is a cannula or a cylinder. The anchor body can have an inner diameter and an outer diameter, wherein the inner diameter ranges from about 1 mm to about 8 mm, and wherein the inner diameter ranges from about 1 mm to about 8 mm.

In some aspects, the diameter of the front plate is substantially the same as the outer diameter of the anchor body. In some aspects, the diameter of the front plate is different than the outer diameter of the anchor body. The diameter of the front plate can be larger than the outer diameter of the anchor body.

The anchor body can have a height of about 0.5 mm to about 3 mm as measured from the bottom of the anchor body to the bottom of the front plate.

The front plate can be curved along the portion of the front plate that is distal to the anchor body. In some aspects the front plate forms a half-sphere.

In some aspects the plurality of haptics are all attached to the anchor body at substantially the same height along the circumference of the anchor body as measured from the bottom of the anchor body. In some aspects, at least two of the plurality of haptics are attached to the anchor body at different heights along the circumference of the anchor body as measured from the bottom of the anchor body. In some aspects, the plurality of haptics are positioned on the anchor body such that plurality of haptics form two groups of haptics, wherein each group comprises at least one haptic, wherein the at least one haptic of the first group is attached to the anchor body along its circumference at a first height and the at least one haptic of the second group is attached to the anchor body along its circumference at a second height, wherein the first and the second height are measured from the bottom of the anchor body and the first and the second height are different.

In some aspects, all components of the Kpro device are flexible.

In some aspects, the Kpro device is implantable using a minimally invasive incision. The minimally invasive incision can be about 3 mm.

In some aspects the anchor body can be configured to couple to a front plate during implantation. In some aspects the anchor body can be a ring having an inner diameter and an outer diameter can range from about 1 mm to about 8 mm, and wherein the inner diameter can range from about 1 mm to about 8 mm. The front plate can include an anterior portion and a posterior stem portion, wherein the stem portion is configured to couple to the anchor body during implantation. The anterior portion of the front plate can be substantially round as measured along a first axis. The stem portion can be a cannula or a solid cylinder and the stem portion can have an outer diameter. The diameter of the anterior portion of the front plate as measured along the first axis can be substantially the same as the outer diameter of the stem portion as measured along the same axis. The diameter of the anterior portion of the front plate as measured along the first axis can be different than the outer diameter of the stem portion as measured along the same axis. The stem portion can be threaded and the anchor body can be configured to be screwed onto the stem during implantation.

In some aspects, at least one of the plurality of haptics can have a hole.

In some aspects, the plurality of haptics can be in a first position prior to implantation and a second position after implantation, wherein the plurality of haptics can be folded in towards the anchor body when in the first position and can be extended radially away from the anchor body when in the second position.

Also described herein is a method of implanting a keraposthesis (Kpro) device as described herein into an eye, wherein the method can include: folding the plurality of flexible haptics in towards the center of the anchor body; inserting the anchor body into the eye through an incision; and un-folding the plurality of flexible haptics such that they extend radially away from the anchor body into a portion of the eye. The incision is a minimally invasive incision. The incision can be about 3 mm or less. In some aspects, the method can further include inserting the front plate into the eye through the incision; and coupling the stem portion of the front plate to the anchor body.

BRIEF DESCRIPTION OF THE DRAWINGS

Further aspects of the present disclosure will be readily appreciated upon review of the detailed description of its various embodiments, described below, when taken in conjunction with the accompanying drawings.

FIGS. 3A-3G shows a top view of non-limiting aspects of a flexible haptic of a Kpro device.

FIGS. 11-12.

FIGS. 11-12.

FIG. 31 is a higher resolution scan of a slightly different cross section of the same eye as 30. This can demonstrate intact cornea in the eye implanted with the Kpro device.

DETAILED DESCRIPTION

Figure 1:
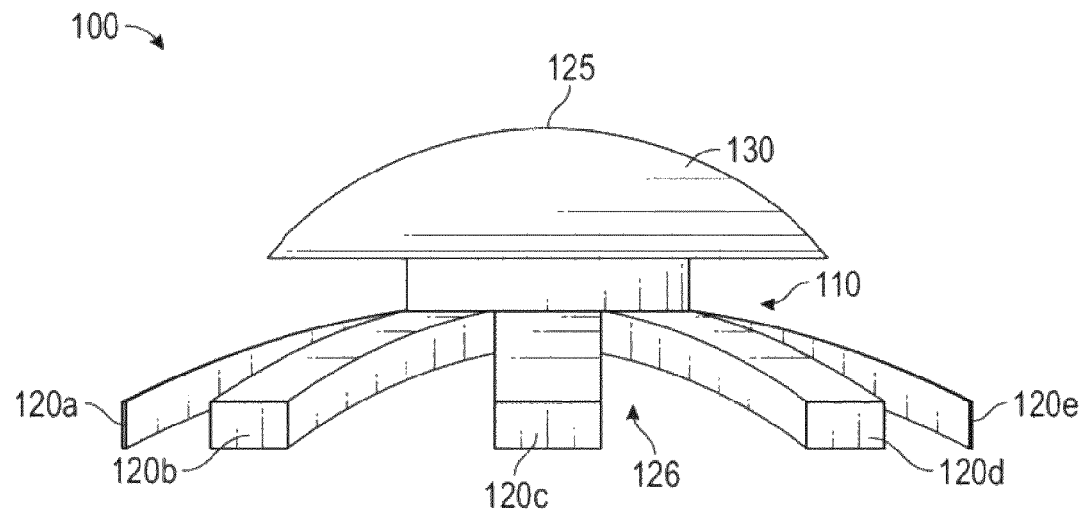
FIG. 1 shows a side view of aspects of a keratoprosthesis (Kpro) device.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', 'less than y', and 'less than z'. Likewise, the phrase 'about x, y, z, or greater' should be interpreted to include the specific ranges of 'about x', 'about y', and 'about z' as well as the ranges of 'greater than x', 'greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Embodiments of the present disclosure will employ, unless otherwise indicated, techniques of molecular biology, microbiology, organic chemistry, biochemistry, physiology, cell biology, cancer biology, and the like, which are within the skill of the art. Such techniques are explained fully in the literature.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, "biocompatible", can refer to a material that along with any metabolites or degradation products thereof that are generally non-toxic to the recipient and do not cause any significant adverse effects to the recipient. Generally speaking, biocompatible materials are materials that do not elicit a significant inflammatory or immune response when administered to a patient.

As used herein, "copolymer" can generally refer to a single polymeric material that is comprised of two or more different monomers. The copolymer can be of any form, such as random, block, graft, etc. The copolymers can have any end-group, including capped or acid end groups.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans).

Unless otherwise indicated, the term "polymer" includes both homopolymers and copolymers (e.g., polymers of two or more different monomers) and oligomers. Similarly, unless otherwise indicated, the use of a term designating a polymer class is intended to include homopolymers, copolymers and graft copolymers.

Discussion

The cornea is makes up the outer anterior layer of the eye. A normal cornea is transparent and curved and focuses light from the outside world through the pupil and lens onto the retina. It is highly innervated, immune privileged, and avascular. The cornea receives nutrients from the tear film outside the eye and aqueous fluid inside the eye. When injured by disease or dysfunction the cornea becomes opaque, causing scattering of light and loss of visual function.

The standard treatment for corneal blindness is corneal transplant surgery. In a corneal transplant, human donor cornea is sutured to the host to replace the damaged host cornea. If there is no significant vascularization of the cornea and corneal stem cells remain intact corneal transplantation can be performed. In corneal transplantation a circular section of diseased cornea is removed and replaced with a circular piece of cornea collected from a deceased donor. Over 40,000 corneal transplantations are done each year. However, in eyes were corneal stem cells have been damaged or there is vascularity, transplantation cannot be performed due to risk of rejection. Additionally, cornea transplants also have an estimated failure rate of about 5-15 percent over the first 5 years. Repeated transplants are at a high risk for rejection.

Currently, in these situations a keratoprosthesis (Kpro) can be an option. The most common Kpro in use is the Boston Keratoprosthesis Type I (BKpro). The BKpro is made of a hard, inflexible acrylic material, polymethylmethacrylate (PMMA). The BKpro contains a 5.5 mm front plat attached to a 3 mm optic. It also includes a backplate of either titanium or acrylic with perforations that can be snapped or screwed onto the front plate. During implantation of the BKpro, the front plate and stem is sandwiched around a donor cornea with the back plate. The entire BKpro apparatus is then sutured into the patient's eye as in a corneal transplant. This allows for the center of the cornea to remain clear even if the donor tissue is otherwise opacified by rejection. The success rate of the BKpro varies from about 50 percent to 70 percent at 3-5 years. Vision loss occurs over time due to complications such as extrusion, infection, and especially membrane formation and glaucoma.

The most common complication of BKpro surgery is glaucoma, reported at a rate of about 60-76 percent. Due to the replacement of the cornea with a rigid Kpro accurate intraocular pressure monitoring becomes impossible. Progressive angle closure due to the presence of the device is also thought to be a possible cause. Many centers now routinely place a glaucoma shunt at the time of Kpro surgery. However, studies report that patients may still loose vision from progressive glaucoma despite the presence of a functioning aqueous glaucoma shunt.

Another common complication of BKpro surgery is retroprosthetic membrane formation. This complication is reported to occur at a rate of about 25 to about 65 percent. While some thin membranes are amenable to laser membrane dissection, thicker membranes can recur repeatedly and lead to vision loss. The cause of membrane formation remains unclear. A molecular analysis has demonstrated cellular origin from both the donor as well as the host cornea. Inflammation is thought to be an important contributory factor. The use of a titanium back plate has been found to anecdotally reduce rate of membrane formation.

Expulsive choroidal hemorrhage is the most feared complication of ocular surgery requiring large open wounds such as those that are needed for BKpro. It usually results in rapid extrusion of ocular contents and total irreversible loss of vision. The complication occurs at a rate of about 0.5 percent. Decreasing the time the eye is open directly correlates to reduced incidence of expulsive choroidal hemorrhage.

While the supply of donor corneal tissue is adequate in the United States, this is not true of most health systems outside of the United States. With only about 150,000 transplants being performed worldwide for an estimated number of patients who would benefit from transplantation numbering in the millions, there is a severe global shortage of donor corneas.

In cases of severe eye surface trauma, such as with chemical or heat burns and certain inflammatory conditions of the eye, the cornea can be come scarred and unable to transmit the light necessary to retain vision. Patients with severe damage are unable to tolerate cornea transplantation. Kpros are used in such situations as they are resistant to tissue scarring.

In view of the shortcomings of current Kpros, described herein are Kpro that can include an anchor body and a plurality of flexible haptics, where the plurality of flexible haptics can be attached to and are capable of extending radially from the anchor body. In some aspects, the Kpro can include a front plate, where the front plate is attached to the anchor body such that the Kpro device is a single implantable device. In some aspects, the anchor body is configured to couple to a front plate during implantation. Also provided herein are methods of using the Kpro device. The Kpro device described herein can be suitable for implantation using minimally invasive techniques. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Figure 2:
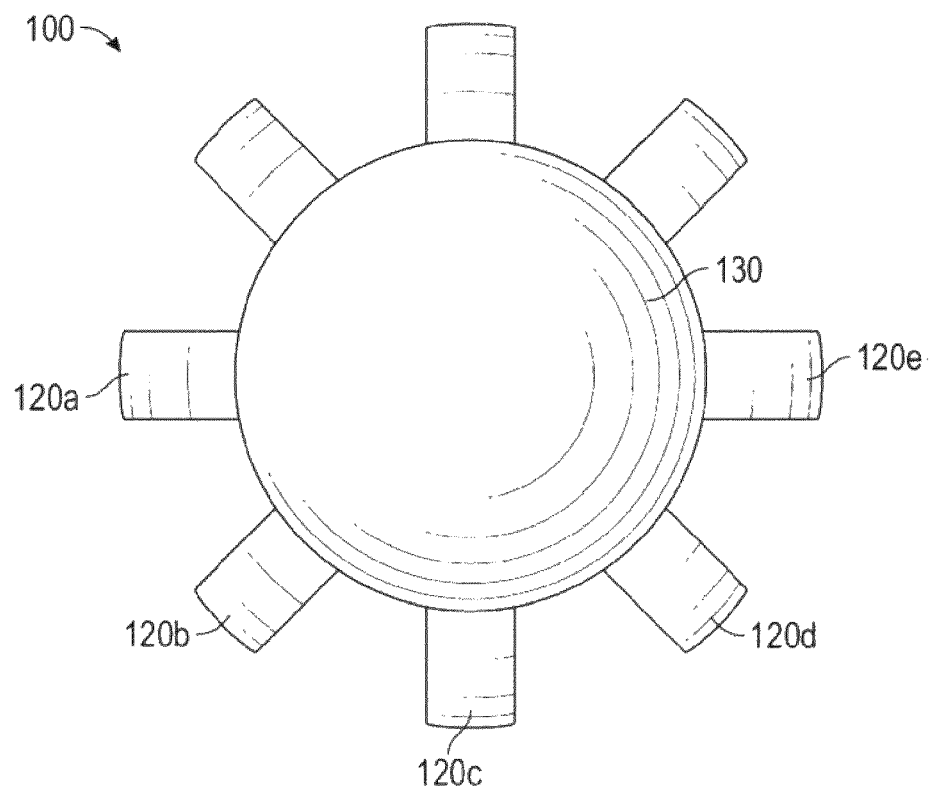
FIG. 2 shows a top view of aspects of the keratoprosthesis device of FIG. 1.
Figure 4A:
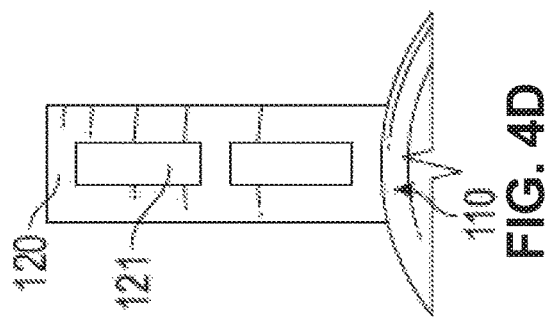
FIGS. 4A-4H shows a top view non-limiting aspects of holes in a flexible haptic of a Kpro device.
Figure 4B:
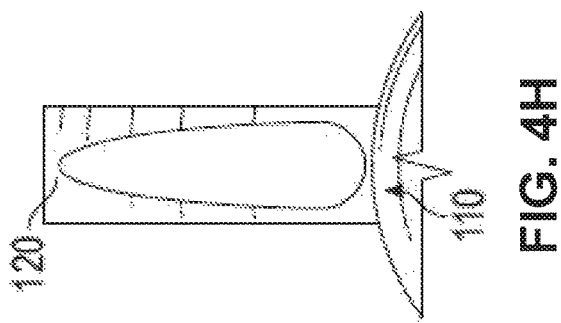
Figure 4C:
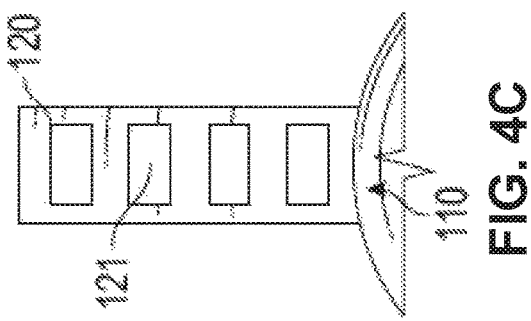
Figure 4D:
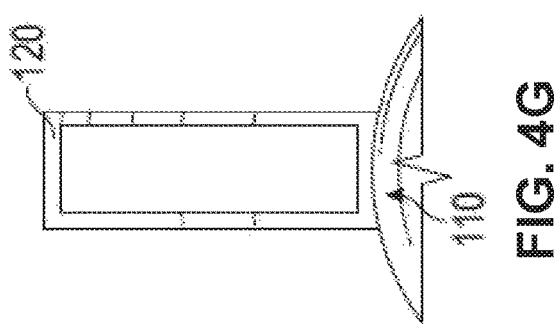
Figure 4E:
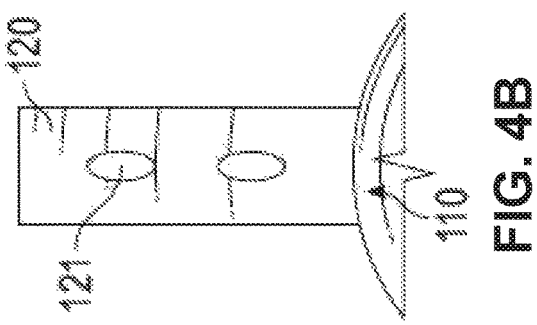
Figure 4F:
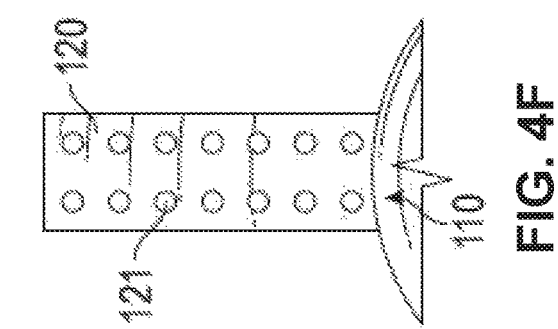
Figure 4G:
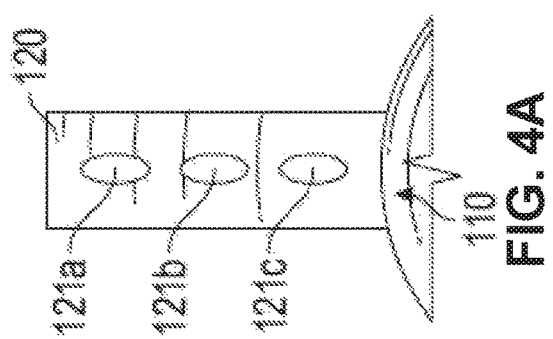
Figure 4H:
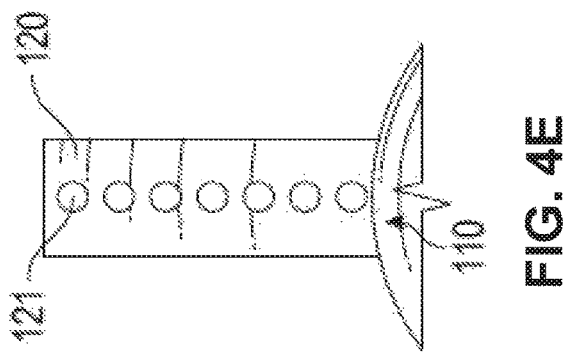

With the general description of aspects of the Kpro devices in mind, attention is directed to FIGS. 1 and 2, which shows a side view (FIG. 1) and a top view (FIG. 2) demonstrating aspects of a keratoprosthesis (Kpro) device 100. The Kpro device 100 can have an anchor body 110 that can include of a plurality of haptics 120a-e (collectively 120). As discussed above, the anchor body 110 can be coupled to a front plate 130. In some aspects, such as those illustrated in FIG. 1, the anchor body 110 can be integrated with the front plate 130 such that the Kpro device is a single uni-body device.

The anchor body 110 can be a cannula, cylinder, or other suitable three dimensional shape and can form a stem 124 that the flexible haptics 120 can be attached. Although the front plate 130 and anchor body 110 can be integrated with one another, the stem 124 can be between the flexible haptics 120 and the front plate 130. The stem 124 can be approximately central with respect to the front plate 130.

The front plate 130 can be curved along its anterior surface 125 (i.e. the forward facing surface of the device when implanted). The front plate 130 can have a diameter that is greater than the stem 124. In some aspects, the front plate 130 can form a half-sphere and can be substantially flat along its posterior surface 126 when the front plate 130 has a larger diameter than the stem 124. In other aspects, the front plate 130 can be curved along its posterior surface. The curves along the anterior 125 and posterior 126 surface of the front plate 130 can have the same angle of curvature. The curves along the anterior 125 and posterior surface 126 of the front plate 130 can have different angles of curvature.

The flexible haptics 120 can be coupled to, integrated with, or otherwise attached to the anchor body 110, such as on the stem 124. The Kpro device can have any number of flexible haptics 120. The number of flexible haptics 120 can be 1, 2, 3, 4, 5, 6, 7, 8, 9, 10, 11, 12, 13, 14, 15, 16, 17, 18, 19, 20, or more. The flexible haptics 120 can be movable along a vertical axis of the Kpro device. In other words, they are capable of being folded up (or down) against and/or beyond the anchor body 110. This is discussed in greater detail with respect to e.g. FIGS. 6-8D and 11-12. The flexible haptics 120 can also be folded, stretched, or otherwise bent along their horizontal, vertical, and/or z-axis. As shown in e.g. FIGS. 1 and 2, the flexible haptics 120 can extend radially outward from the anchor body 110. It will be appreciated that the distance the flexible haptics 120 extend outward from the anchor body 110 will vary based on their positioning relative to (e.g. folded up, down, or in an intermediate position against and/or beyond) the anchor body 110. For example, if the flexible haptics are folded up (or down) such that their horizontal axis is substantially vertical with respect to the anchor body 110, they may not extend beyond the front plate 130 and when the flexible haptics 120 are in an intermediate position they can extend beyond the front plate as shown in FIG. 2. This is discussed in greater detail with respect to e.g. FIGS. 6-8D and 11-12.

The flexible haptics 120 can have any suitable shape and contour. FIGS. 3A-3G shows several non-limiting suitable shapes and contours. Other shapes will be appreciated by those of skill in the art based on the description and figures herein. As shown in e.g. FIGS. 4A-4H, the flexible haptics 120 can include one or more holes 121a, b, c, (collectively 121). It is noted that the flexible haptics 120 in FIGS. 4A-4H are shown in one shape for reference only and that the hole(s) 121 can be on any shape or size flexible haptics 120. The hole(s) 121 can be any suitable shape or size. Suitable shapes include regular shapes and regular polygons (e.g. circles, ellipses, squares, triangles, hexagons, octagons, and rectangles) and irregular shapes and polygons. The hole(s) can, inter alia, allow for diffusion of nutrients from the eye fluids into the cornea so that there is no breakdown of the tissue from lack of nutrients. The number of holes on each haptic can be 0 (no holes), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 59, 59, 60 or more holes. The holes can be positioned anywhere on the flexible haptics 120. Holes can be placed to minimize area of cornea covered by the arms. Thus, in some aspects, the hole(s) 121 can be placed in the center away from the edges of the flexible haptics 120. In some aspects the hole(s) can be substantially circular or oval to reduce stress points.

The flexible haptics 120 included in any given Kpro device can be all the same (e.g. the same shape, same number of holes, same size, and the same in any other characteristic). In other aspects, at least two of the flexible haptics are different (e.g. different in at least one characteristic (e.g. shape, size, material, number of holes or any other characteristic) from each other. Where all the haptics are the same, the haptics of the device can be said to be homogenous. In some aspects, at least 3, 4, 5, 6, 7, 8, 9, 10, 11, 12, 13, 14, 15, 16, 17, 18, 19, 20, or more are different from each other. Where at least two of the haptics are different, the haptics of the device can be said to be heterogeneous.

Figure 5:
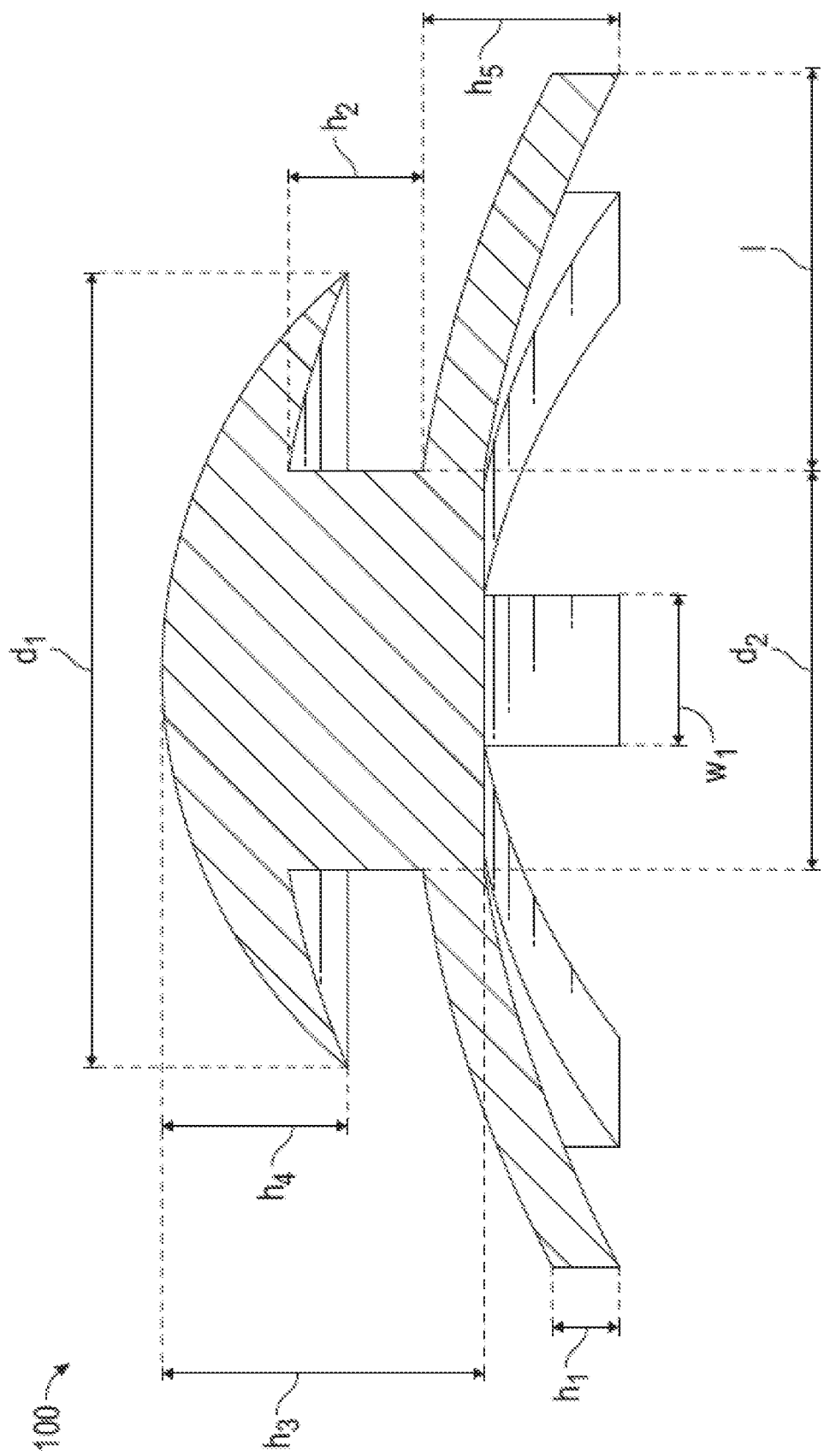
FIG. 5 shows a section view of several aspects of the Kpro device of FIG. 1.

FIG. 5 shows a section view of several aspects of the Kpro device of FIG. 1. The front plate 130 can have a diameter ($d_1$). The diameter ($d_1$) of the front plate 130 can range from about 2 mm to about 10 mm. The diameter ($d_1$) of the front plate 130 can be about 2, 3, 4, 5, 6, 7, 8, 9, or about 10 mm. The anchor body 110 and/or the stem 124 can have an outer diameter ($d_2$). $d_2$ can range from about 1 mm to about 8 mm. The anchor body 110 and/or the stem 124 can be about 1, 2, 3, 4, 5, 6, 7, or about 8 mm in diameter ($d_2$). In aspects where the anchor body 110 and/or the stem 124 is a cannula, the anchor body 110 and/or stem 124 can have an inner diameter, which is the diameter of the void of the cannula as measured at the widest portion between the inner wall of the cannula. The inner diameter can be less than the outer diameter of the anchor body 110 and/or stem 124. The inner diameter of the anchor body 110 can range from about 1 mm to about 8 mm. The inner diameter of the anchor body 110 can be about 1, 2, 3, 4, 5, 6, 7, or about 8 mm in diameter. The anchor body 110 and/or stem can be any shape. In some aspects the anchor body 110 and/or stem is substantially round (circular).

The anterior portion of the front plate 110 can have a height ($h_4$) that is measured from the start of a stem 124 (regardless if the stem is considered part of the front plate 130 or the anchor body 110) to the top of the front plate 130. $h_4$ can range from about 1 mm to about 5 mm. In some aspects, $h_4$ can be about 1, 2, 3, 4, or about 5 mm, The Kpro device 100 can have a height ($h_3$) that is measured from the bottom of the anchor body 110 to the top of the front plate 130. $h_3$ can range from about 0.1 mm to about 8 mm. $h_3$ can be about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, or about 8 mm. The stem 124 (whether the stem be considered part of the front plate 130 or the anchor body 110) can have a height ($h_2$). $h_2$ can range from about 0.1 mm to about 2 mm. $h_2$ can be about 0.1, 0.2, 0.3, 0.4, 0.5, 0.6, 0.7, 0.8, 0.9, 1, 1.2, 1.3, 1.4, 1.5, 1.6, 1.7, 1.8, 1.9, or about 2 mm.

The flexible haptics 120 can have a height ($h_1$), a width ($w_1$), a length (l, FIGS. 3-4), and a reach (r). $h_1$ can range from about 0.1 mm to about 3 mm. $h_1$ can be about 0.1, 0.2, 0.3, 0.4, 0.5, 0.6, 0.7, 0.8, 0.9, 1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or about 3 mm. $w_1$ can range from about 0.1 mm to about 3 mm. $w_1$ can be about 0.1, 0.2, 0.3, 0.4, 0.5, 0.6, 0.7, 0.8, 0.9, 1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or about 3 mm. r can range from about 0.1 mm to about 6 mm. r can be about 0.1, 0.2, 0.3, 0.4, 0.5, 0.6, 0.7, 0.8, 0.9, 1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or about 6 mm. The length of the flexible haptics 120 refers to the physical length of the flexible haptics 120, whereas the reach (r) can refers to the distance between the outer wall of the anchor body 110 and the end of a flexible haptic 120 when in a specific position. As discussed elsewhere herein, the flexible haptics 120 are movable along the anchor body 110 such that they can be folded up against, completely extended out from, or somewhere in between the anchor body 110 and/or stem 124. Thus, it will be appreciated that the reach will vary based, inter alia, the angle at which the flexible haptic 120 is extended from the anchor body 110 and/or stem 124. The flexible haptics 120 can each have a height ($h_5$) that can be measured from the bottom distal end (end of the haptic farthest from the anchor body 110 and/or stem 124) of the flexible haptic 120 to the point at which the proximal end (end that is attached to, integrated with, and/or otherwise coupled to the anchor body 110 and/or stem 124). $h_5$ can range from about 0.1 mm to about 5 mm. $h_5$ can be about 0.1, 0.2, 0.3, 0.4, 0.5, 0.6, 0.7, 0.8, 0.9, 1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0 mm.

Figure 6:
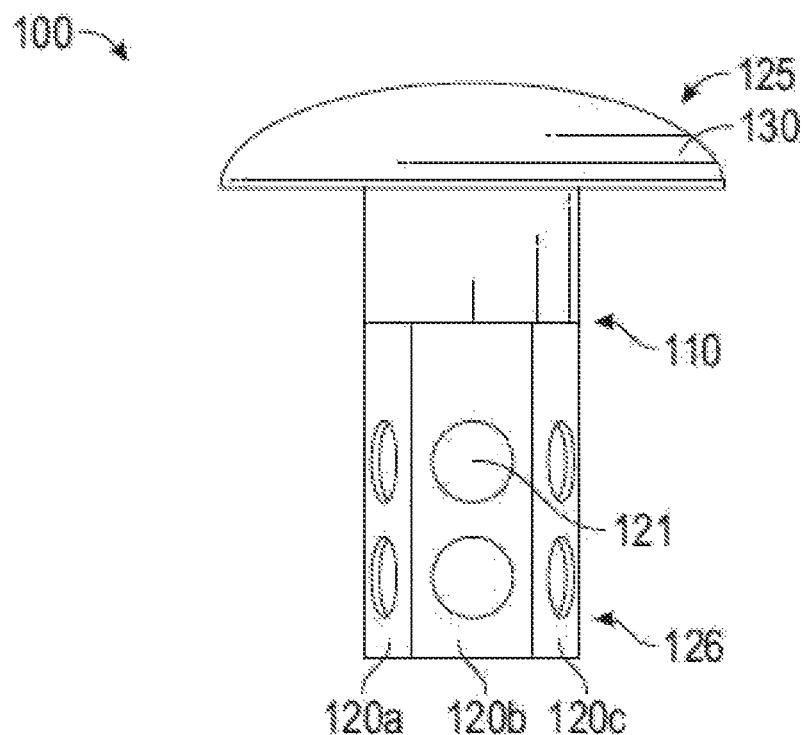
FIG. 6 shows a side view of aspects of a Kpro device with flexible haptics in a closed position.
Figure 7:
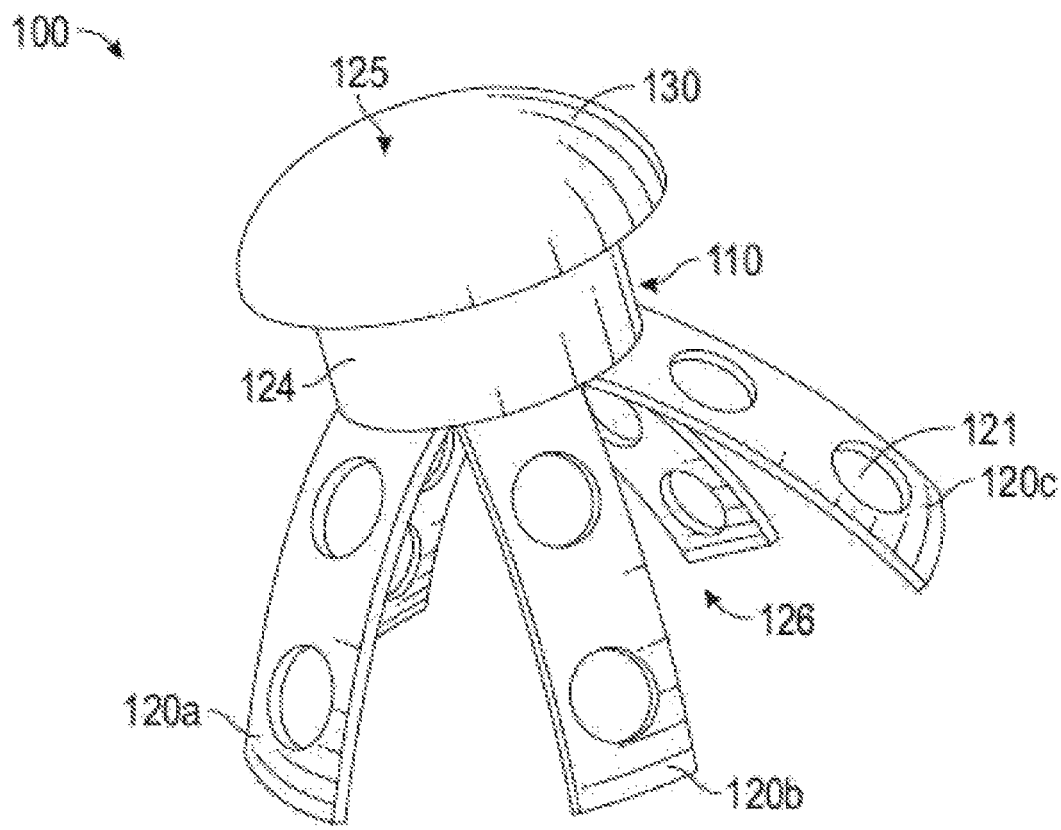
FIG. 7 shows a perspective view of aspects of the Kpro device of FIG. 7 in an open position.
Figure 8A:
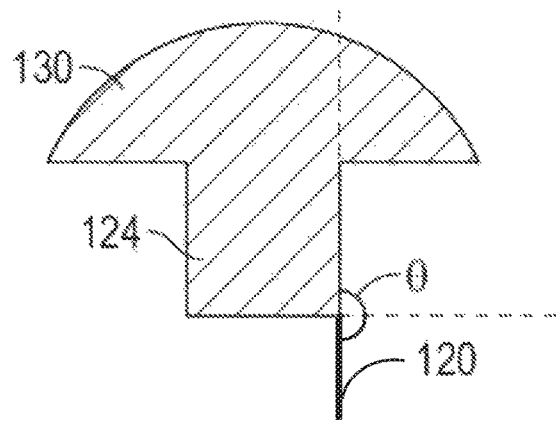
FIGS. 8A-8E show sectional side views of aspects of the Kpro device and positions of flexible haptics across a continuum from open to closed.
Figure 8B:
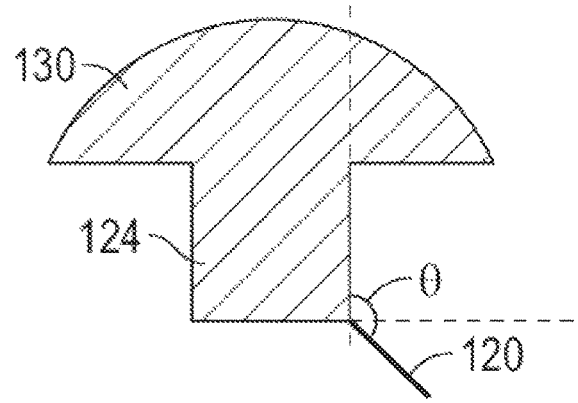
Figure 8C:
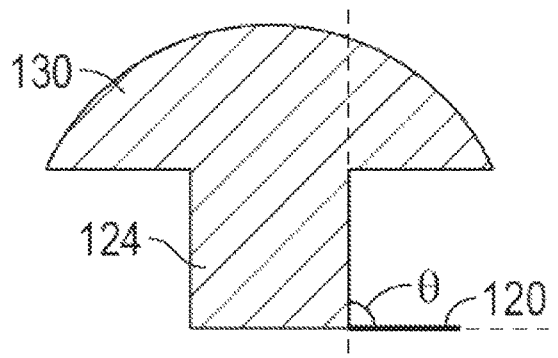
Figure 8D:
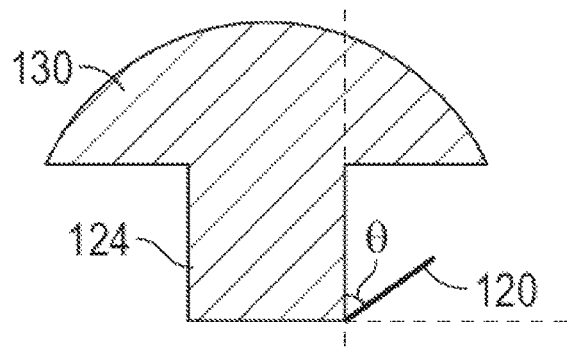
Figure 8E:
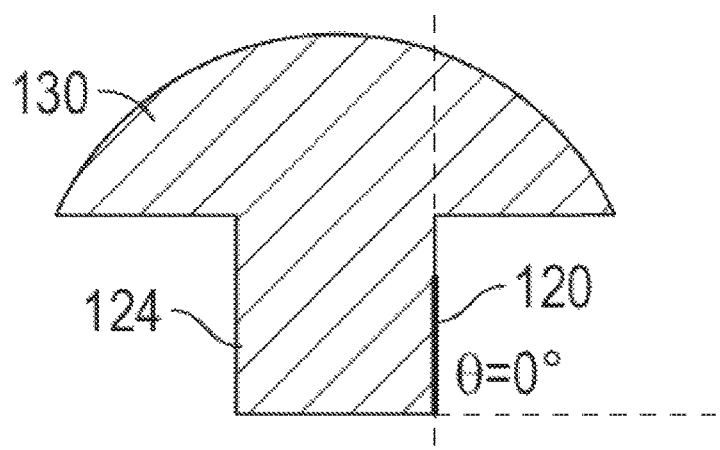

Attention is now directed to FIGS. 6-15, which show various aspects of the Kpro device and its operation. Starting with FIGS. 6-7, which shows a side view of aspects of a Kpro device with flexible haptics 120 in a closed position, the Kpro device can be configured such that the flexible haptics 120 can be in a "closed" position and substantially in line and/or flush with the outer wall of the anchor body 110. The Kpro device can be maintained in the closed configuration during e.g. storage and during implantation. In use, the distal ends of the flexible haptics 120 of the Kpro device in a closed configuration can be inserted through an incision in the eye. After passing through the incision the flexible haptics 120 can be expanded and moved into an "open" configuration, which is shown in FIG. 7. As shown in FIG. 7, the flexible haptics can be expanded such that they extend radially outward from their point of attachment to the anchor body 110.

FIGS. 8A-8E shows a side sectional view of the Kpro device of FIGS. 6-7 that can demonstrate the range of mobility of the flexible haptics 120. For clarity only one flexible haptic is shown in these figures. The flexible haptics 120 can be movable and can range about 180 degrees from vertical. The flexible haptics 120 can be moved from being extended beyond and inline with and/or flush with the stem 124 (FIGS. 8A and 8E, respectively) to fully expanded (FIG. 8C) to being fully extended in line with the outer wall of the stem 124 and/or anchor body 110 (FIG. 8D) and through any degree therein (e.g. FIG. 8C). It will be appreciated that the flexible haptics 120 can be configured to have a limited range (e.g. less than the 180 degrees). This can be controlled e.g. by the material used, contour, shape, width, inclusion of and/or number of holes, etc. Thus, the range of the flexible haptics can be 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, to about 180 degrees.

Figure 9:
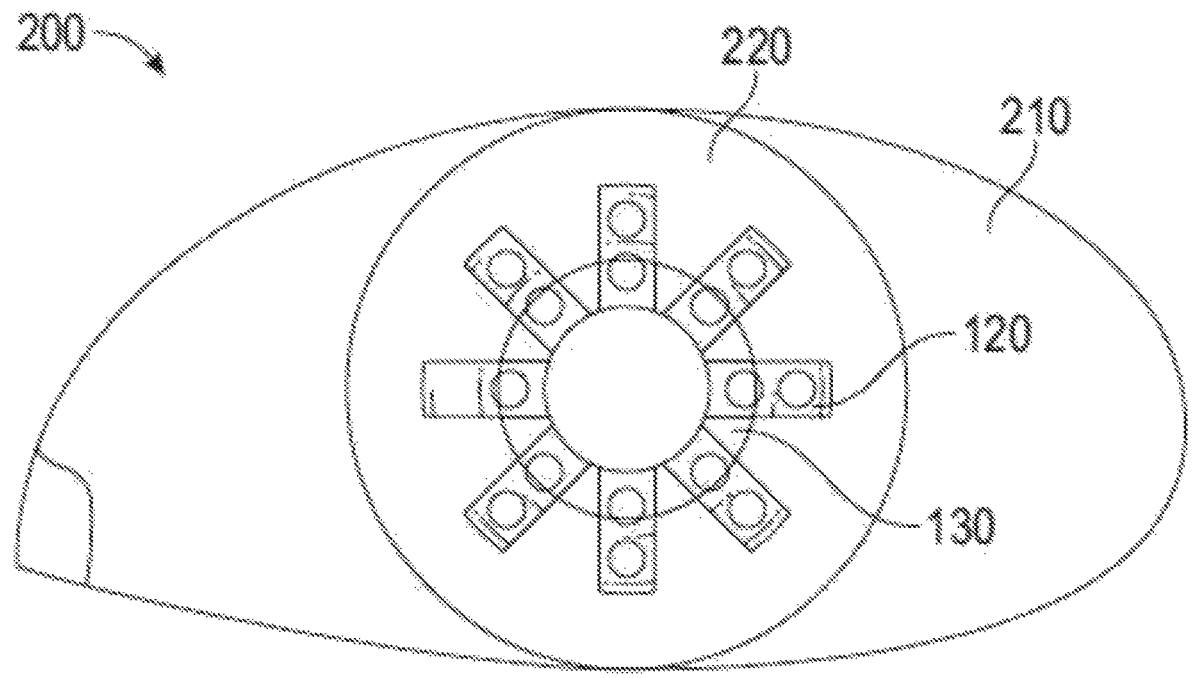
FIG. 9 shows a front view of aspects of the Kpro device of FIG. 1 when implanted in an eye.
Figure 10:
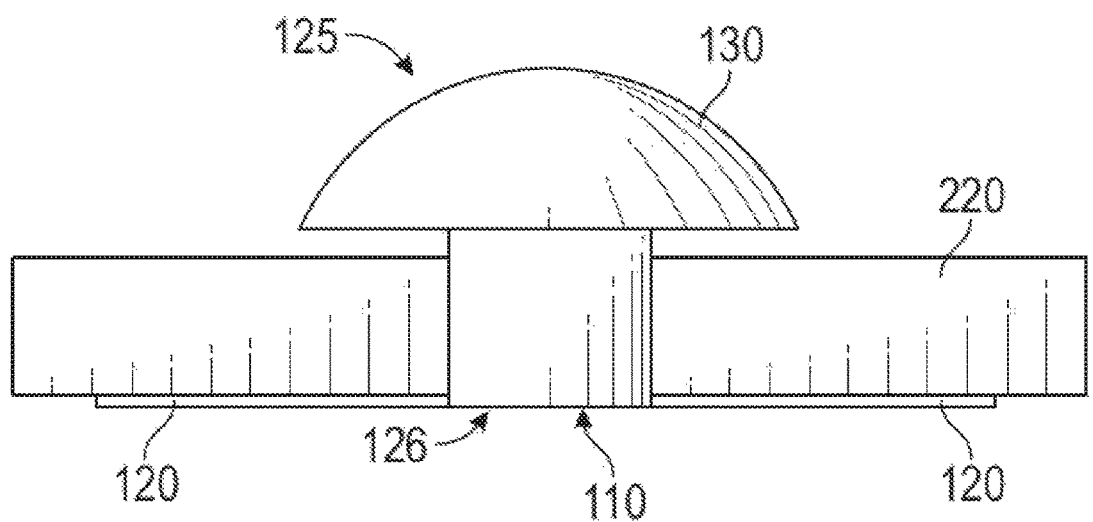
FIG. 10 shows a side sectional view of aspects of the Kpro device of FIG. 1 when implanted in an eye.
Figure 11:
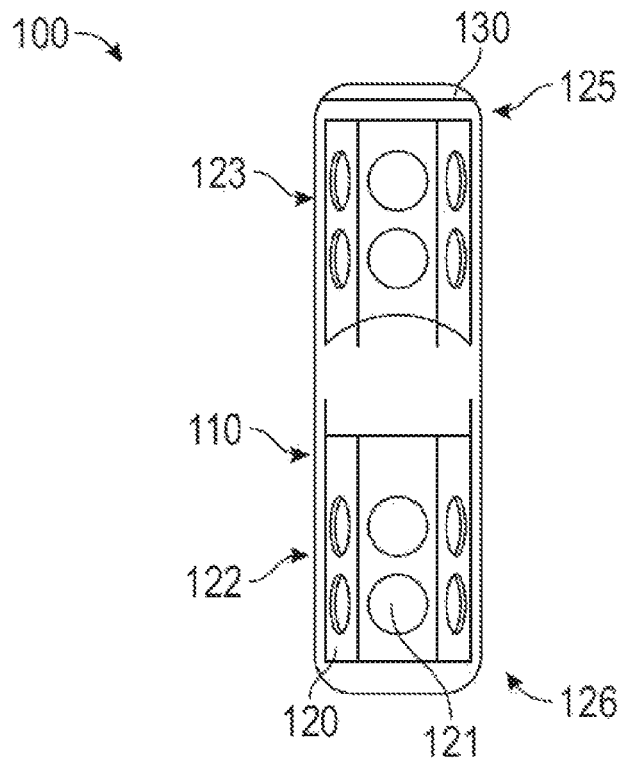
FIG. 11 shows a side view of aspects of a Kpro device having two levels of flexible haptics in a closed position.
Figure 12:
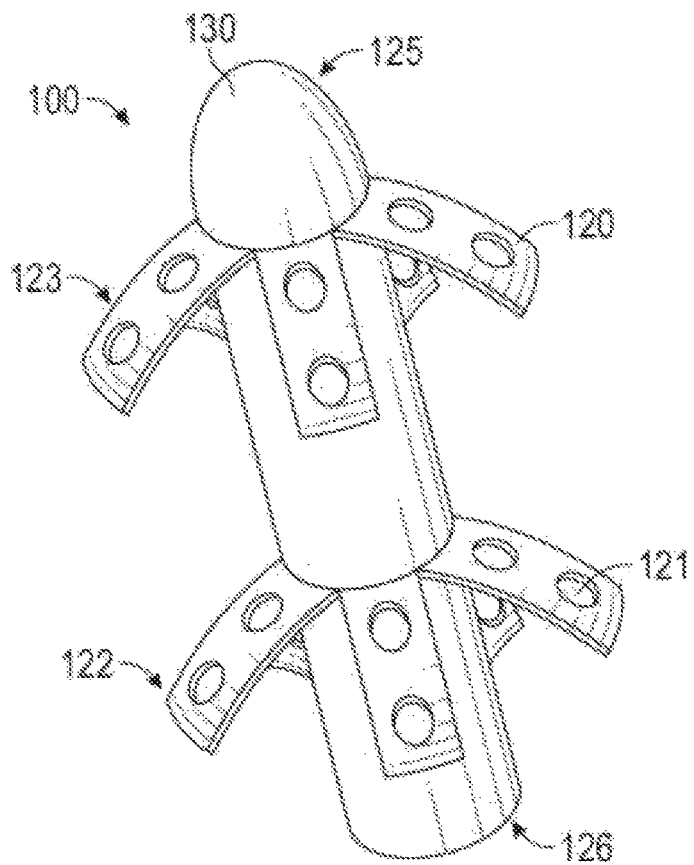
FIG. 12 shows a perspective view of aspects of the Kpro device of FIG. 11 in an open position.

As shown in FIGS. 9-10, the Kpro device 200 can be placed such that the flexible haptics can be expanded into the anterior portion of the eye. The front plate 130 can be placed on the surface of the eye.

Figure 13:
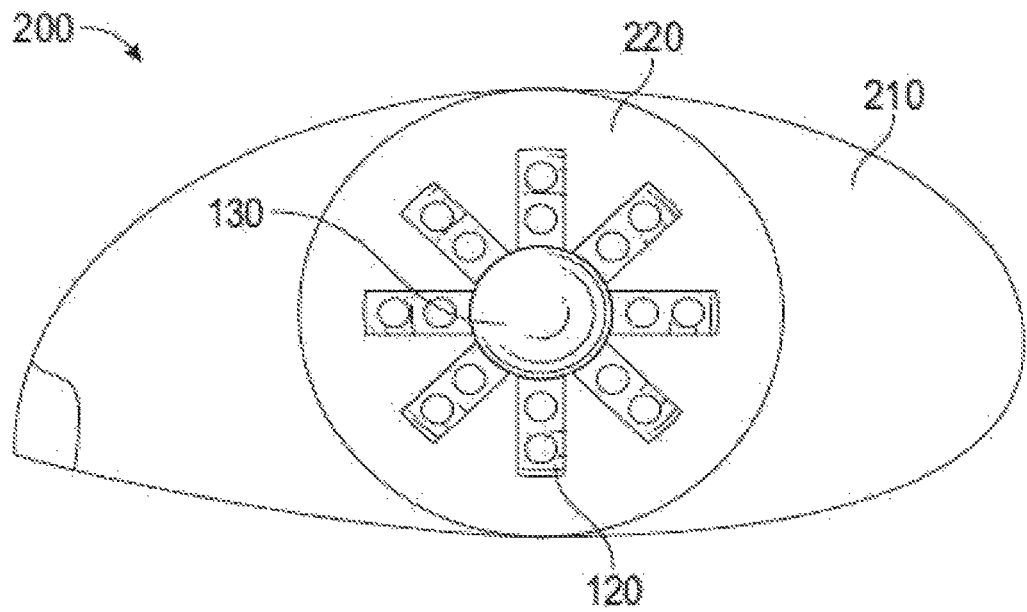
FIG. 13 shows a front view of an eye that is implanted with the Kpro device shown in e.g.
Figure 14:
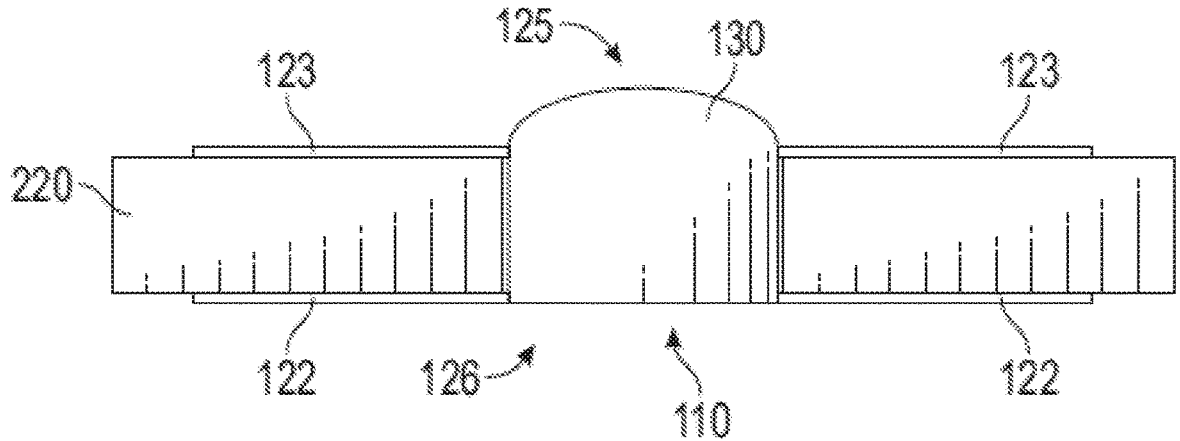
FIG. 14 shows a side sectional view of an eye that is implanted with the Kpro device shown in e.g.
Figure 15:
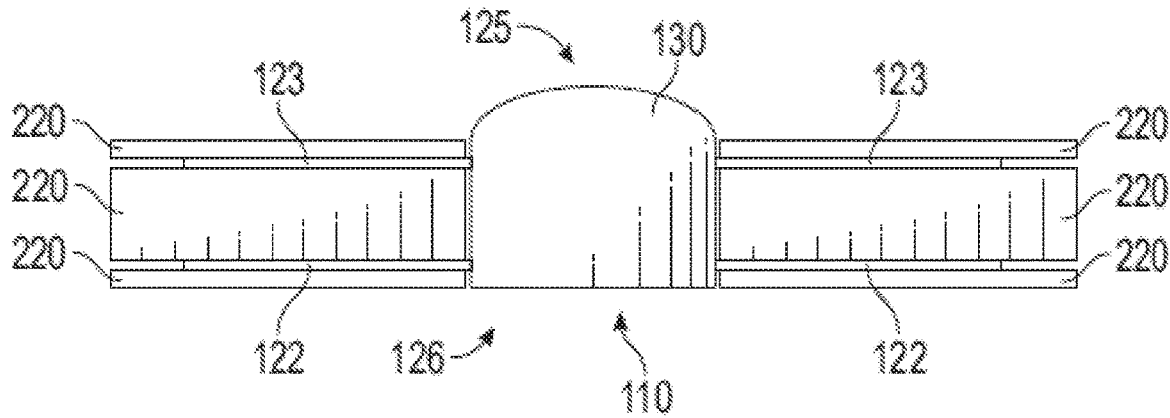
FIG. 15 shows a side sectional view of an eye that is implanted with the Kpro device shown in FIGS. 11-12 using an intralamellar positioning.

In some aspects, the Kpro device 200 can contain more than one level (or group) of flexible haptics 120, 220. As shown e.g. in FIGS. 11-12, the Kpro device 100 can include a first level (or group) of flexible haptics 120, where all the proximal ends of the flexible haptics 120 within each level (or group) 122, 123 are attached at the same height around the anchor body 110 and/or stem 124. Like as discussed with respect to FIGS. 6-7, the first group 122 and the second group 123 of flexible haptics 120 can be movable such that the Kpro device 100 can be in a closed configuration (see e.g. FIG. 11) or an open positions (see e.g. FIG. 12). The Kpro device 100 can be maintained in the closed configuration during e.g. storage and during implantation. In use, the distal ends of the flexible haptics 120 of both the first group 122 and the second group 123 of the Kpro device 100 in a closed configuration can be inserted through an incision in the eye. After passing through the incision the flexible haptics 120, 220 can be expanded and moved into an "open" configuration, which is shown in FIGS. 13-15. As shown in FIG. 13, the flexible haptics 120 can be expanded such that they extend radially outward from their point of attachment to the anchor body 210.

The first group 122 of flexible haptics 220 can be coupled to the anchor body 110 and/or stem 124 such that when they are expanded during implantation they are expanded into the anterior region of the eye (see e.g. FIG. 14) or into the lamellar region (see e.g. FIG. 15). The second group 123 of flexible haptics 120 can be coupled to an anchor body 110 and/or stem 124 at a position such that when the flexible haptics 120 are expanded they are expanded onto the surface of the eye (see e.g. FIG. 14) or into the lamellar region (see e.g. FIG. 15) at a different position than the first group 122 of flexible haptics 120.

Where more than one group of flexible haptics 120, 220 are included in the Kpro device 100, 200 the shape of the front plate does not necessarily have to assist with keeping the device in place in the eye. This is because the additional group(s) of flexible haptics 220 can assist with keeping the device in place as shown in e.g. FIGS. 14-15. As such, in some aspects the shape of the front plate can be such that the diameter of the front plate is substantially the same as the diameter of the stem 124 and/or anchor body 110, 210 as shown in e.g. FIGS. 11-15.

Current Kpro devices are rigid and not reconfigurable as are the Kpro devices described herein. As such, current Kpro devices require an incision large enough to pass the entire width of the device through. This is typically about 9 mm or more. In contrast, due at least to the flexibility of the flexible haptics and/or their attachment to the anchor body 110, the incision can be smaller because it no longer must be sized to the maximum dimension of the anchor portion of the device. Instead, a smaller (minimally invasive) incision can be used because the width that must be passed through the incision is smaller than the final width once the flexible haptics 120 are expanded in place. The Kpro device 100 described in here can be implanted using about a 3 to about 4 mm trephination. This is the case whether the Kpro device 100 described herein are being implanted into the anterior chamber (e.g. FIGS. 9-10) or intralamallerly (e.g. FIGS. 12-13). Additionally, the Kpro devices described herein can remove the need for donor cornea tissue.

As discussed, the Kpro device 100 can be a unibody design where all components are attached to, integrated with, and/or otherwise coupled to each other such that the device is a single unit in its implanted or non-implanted state. This configuration has the advantage in that there is only one part to handle during implantation, which can allow for a faster and more efficient implantation procedure. However, it will be appreciated that the Kpro device 100 can also be configured with separable pieces that can be assembled together e.g. during implantation. The Kpro device 100 with separable pieces can include an anchor body 110 that has flexible haptics 120 and is configured to couple to a front plate 130 during implantation.

Figure 16A:
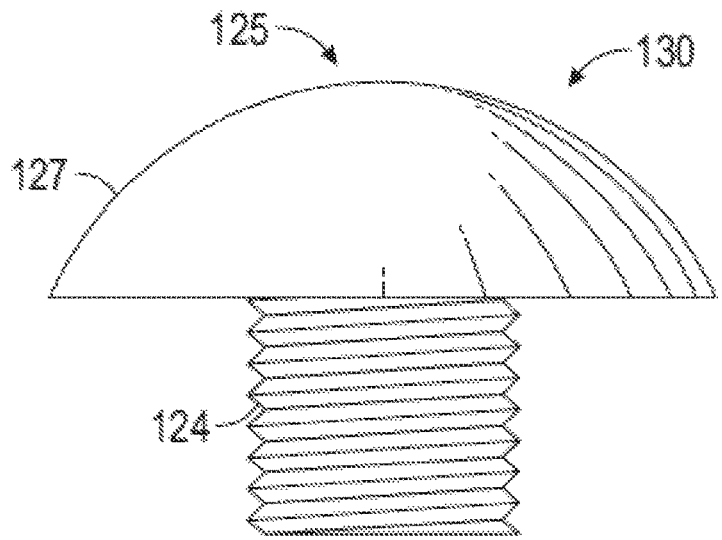
FIGS. 16A-16C shows a side view of non-limiting aspects of front plates that can be part of a Kpro device.
Figure 16B:
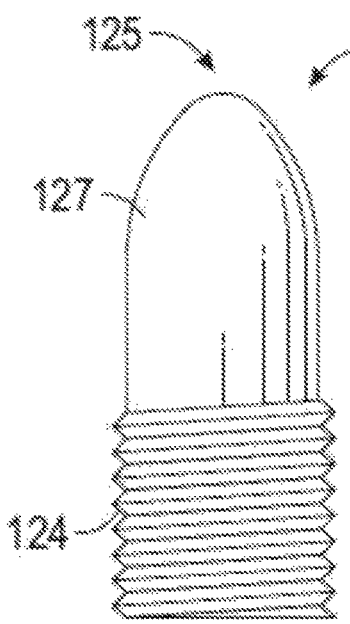
Figure 16C:
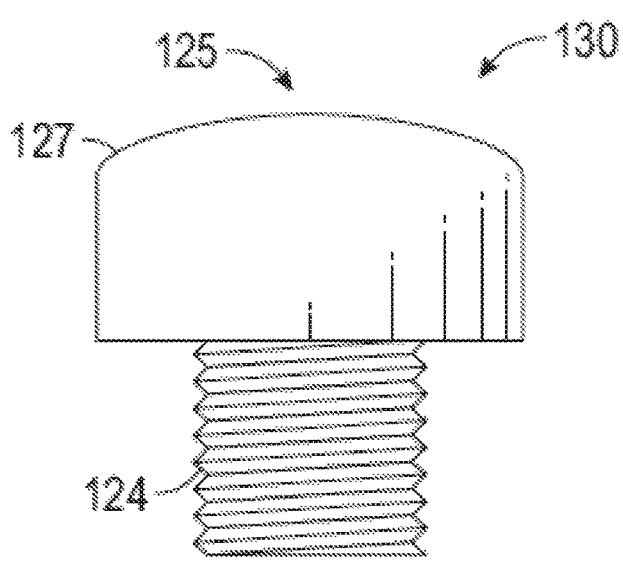
Figure 17A:
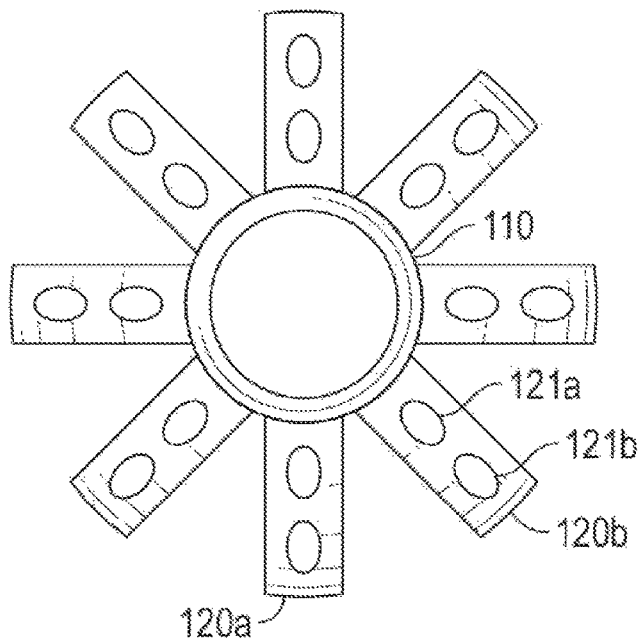
FIGS. 17A-17O shows a top view of non-limiting aspects of the posterior anchor that can be used with a font plate as shown in FIG. 16.
Figure 17B:
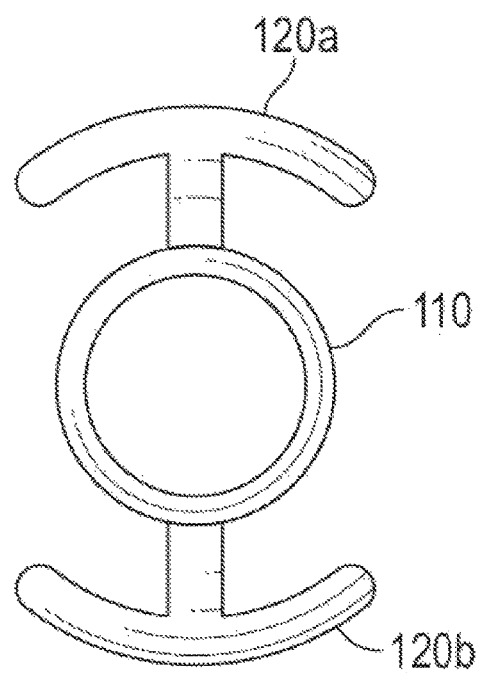
Figure 17C:
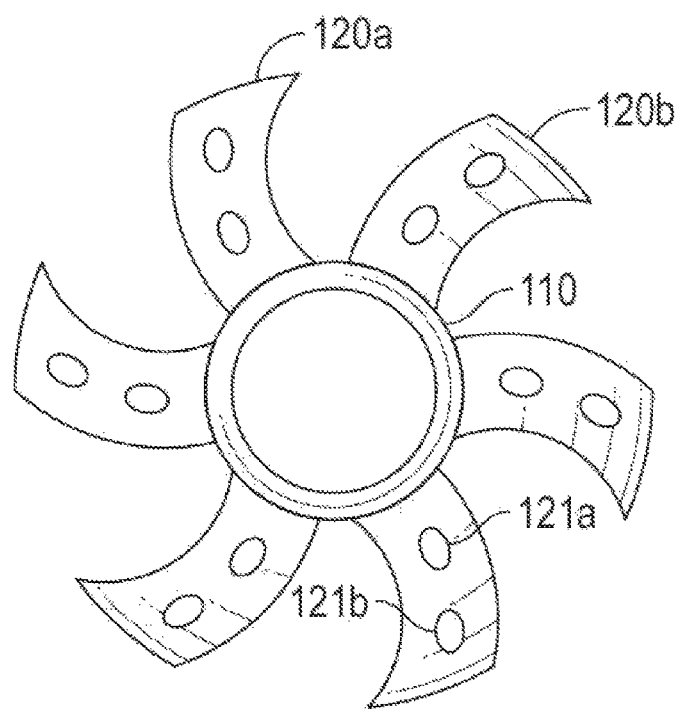

Discussion of the Kpro device 100 now continues with FIGS. 16A-16C, which shows non-limiting aspects of a front plate 130 that can be part of a Kpro device 100 that can be configured with separable pieces. The front plate 130 can include a top portion 127 and a stem 124 that can be integrated, attached, or otherwise coupled to each other. The stem 124 can include threads (left or right handed) that can extend up a portion or the entirety of the stem 124. The stem 124 can be configured to couple to the anchor body 110 vial the threads. FIGS. 17A-17C shows non limiting aspects of the anchor body 110 that can be configured to couple to the front plate 130. The anchor body 110 can be configured as a ring or cannula. The anchor body 110 can have an inner diameter and an outer diameter ranges from about 1 μm to about 8 m, and wherein the inner diameter ranges from about 1 μm to about 8 mm. The outer diameter of the anchor body 110 can be about 1, 2, 3, 4, 5, 6, 7, or about 8 mm. The inner diameter of the anchor body 110 can be about 1, 2, 3, 4, 5, 6, 7, or about 8 mm. The thickness of the anchor body 110 can be the difference between the inner and outer diameters. The thickness, of the anchor body 110, in some aspects, can range from about 0.1 mm to about 2 mm. The thickness of the anchor body 110, in some aspects, can be about 0.1, 0.2, 0.3, 0.4, 0.5, 0.6, 0.7, 0.8, 0.9, 1, 1.2, 1.3, 1.4, 1.5, 1.6, 1.7, 1.8, 1.9, or about 2 mm. The anchor body 110 can have a height. The height can be measured as the length of the anchor body along the plane that is perpendicular to the plane that the thickness is measured. The height of the anchor body 110 can range from about 0.5 to about 3 mm. The height of the anchor body 110 can be about 0.5, 0.6, 0.7, 0.8, 0.9, 1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or about 3 mm.

Flexible haptics 120 can be attached to, integrated with, or otherwise coupled to the anchor body 110. The anchor body 110 can be configured to receive the stem 124 of the front plate 130. The anchor body 110 can include threads (right or left handed). In some aspects, the threads can be present on the inner wall or surface of the anchor body 124. The flexible haptics 120 can be movable along the vertical axis such that they can fold up to reduce the overall diameter of the anchor body 110 similar to that previously described with respect to e.g. FIGS. 8A-8E.

During implantation, one or more anchor bodies 110 configured to couple to a front plate 130 can be in a closed position and inserted through an incision and placed in the anterior region of or intralamellarly in the eye similar to the placement shown in e.g. FIGS. 10, 14, and 15. Once in position, the flexible haptics 120 can be expanded from the closed configuration to the open configuration to position the anchor body(ies) 110 in place. After placement of the anchor body(ies) 110 in the eye, the front plate 130 can be positions such that the stem 124 is passed into the incision and is coupled with the anchor body(ies) already implanted. Insofar as the anchor body(ies) 110.

The Kpro device 100 or any part thereof can be made of a suitable material. The suitable material can be flexible. The degree of flexibility can vary from easily bendable and/or stretchable to difficult to bend or stretch. Some components of the Kpro device 100 can be more or less flexible than others. All the components of the Kpro device 100 can be made of the same material. In some aspects, at least two of the components of the Kpro device 100 are made of different materials. The material can be transparent or substantially transparent. The material can be optically transparent. The material can be biocompatible.

The material can be a polymer. The polymer can be a synthetic polymer. The polymer can be a natural polymer. The polymer can be a copolymer. The polymer can be a cross-linked polymer. Non-limiting examples of polymers can include an acrylate polymer, polyvinyl chloride, polyolefin copolymers, fluoropolymers (e.g. polytetrafluoroethylene (PTFE), polyamides, polyimides, polyesters, polyurethane, copolymers thereof, and combinations thereof.

Acrylate polymers can include those formed from the following monomers: methacrylates, methyl acrylate, ethyl acrylate, 2-chloroethyl vinyl ether, 2-ethylhexyl acrylate, hydroxyethyl methacrylate, butyl acrylate, butyl methacrylate, and TMPTA. The acrylate polymer can be or include poly(methylmethacrylate) (PMMA), phenylethyl acrylate (PEA), phenylethyl methacrylate (PEMA).

The material can be silicone, a cross-linked silicone polymer or copolymer, acrylic polymer or copolymer, and any suitable combination thereof.

The Kpro devices 100 can be implanted into an eye to treat a condition of the eye in a subject. Non-limiting examples of eye conditions that can be treated using a Kpro device 100 can include corneal blindness, scarring, vascularization, opacity, distortion, thinning, and/or swelling.

Where two or more polymers and/or other materials are included, the amount of the first polymer or material can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or about 99.9% by weight and the amount of the second, third, fourth, fifth, or sixth polymer and/or material. Each polymer or material included can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, or 99.9% by weight of the component.

In some aspects, all the components of the Kpro device 100 (and thus the Kpro device 100 are made of the same polymer or material.

Implantation of the Kpro device 100 can include placing the subject under anesthesia (e.g. general, regional anesthesia, conscious sedation, and combinations thereof). The eye can be prepped and draped in a sterile manner. For example, the eye and area can be sterilized using, for example, a 5% iodine preparation. Suitable eye preparation and sterilization techniques will be appreciated by those of ordinary skill in the art. A small incision or side port incision (about 0.5 to 2 mm) can be made in the periphery of the cornea to allow instillation of a viscoelastic jelly into the eye to maintain the pressure and shape of the eye during subsequent steps. A circular incision matching the size of the stem 124 and/or anchor body 110 of a Kpro device 100 described herein can be made in the eye using a suitable cutting device. Suitable cutting devices include, but are not limited to, a circular knife, trephine, biopsy punch, or laser (e.g. a femtosecond laser). This minimally invasive incision can be about 3 mm (typically about 2-4 mm). The Kpro device 100 can be examined for defects. The flexible haptics 120 can then be flexed together into their closed position. The closed position can be held, for example, by suturing one or more parts of the Kpro device 100 to each other (e.g. with a slipknot suture or other method that allows for easy release) or by a surgical instrument. The Kpro device 100 can then be inserted through the circular incision with the flexible haptics 120 and/or anchor body 110 leading. The flexible haptics 120 can then be released and expanded into an open or partially open configuration. The flexible haptics 120 can then hold the Kpro device 100 in place. Any remaining viscoelastic jelly can be removed via draining out the side port incision.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 18A:
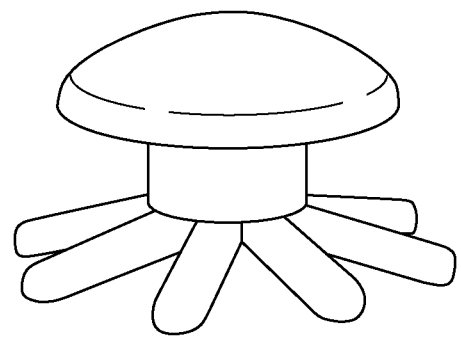
FIGS. 18A-18O show images of a unibody Kpro device having deployable flexible haptics that is suitable for minimally invasive surgical techniques.
Figure 18B:
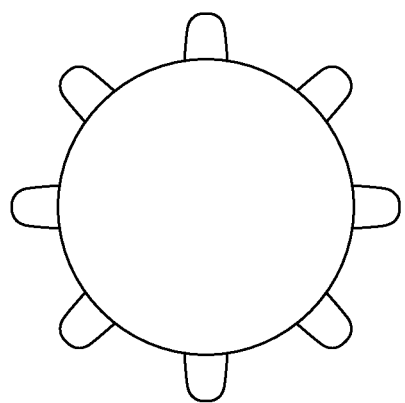
Figure 18C:
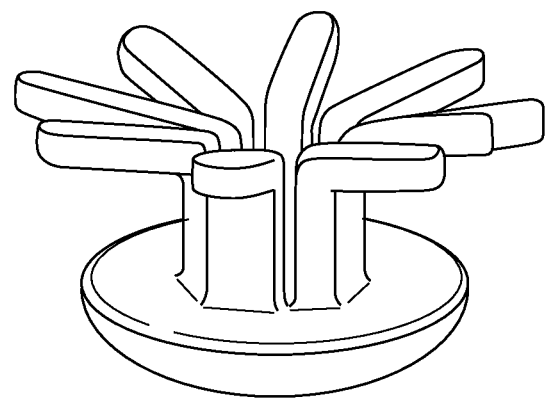

A uni-body minimally invasive Kpro device having an anchor body with deplyoable flexible haptics was designed. FIGS. 18A-18O show images of a unibody Kpro device having deployable flexible haptics that is suitable for minimally invasive surgical techniques. FIG. 18A shows a perspective view where the Kpro device is sitting with the haptics on the bottom and the front plate at the top. FIG. 18B shows a top view of the uni-body Kpro device shown in FIG. 18A. FIG. 18C shows another perspective view of the Kpro device where the Kpro device is upside down as compared to that shown in FIG. 18A.

Example 2

Figure 19A:
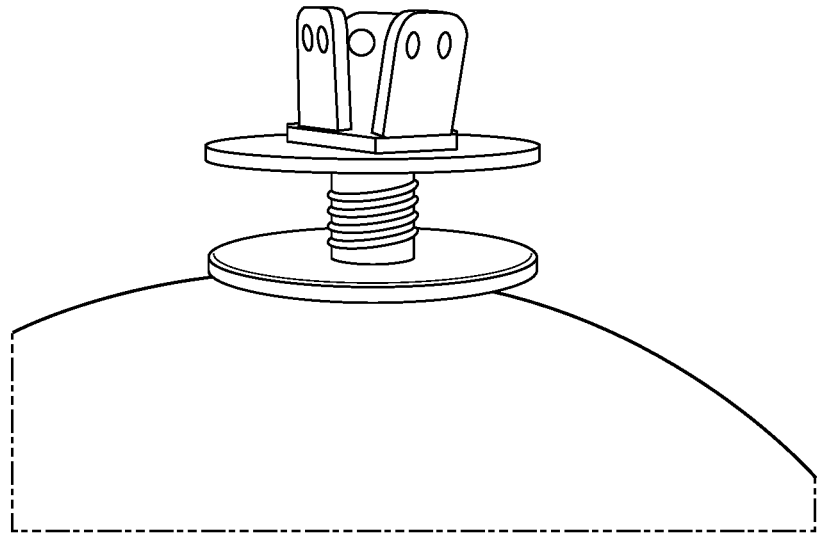
FIGS. 19A-19C show images of a two-part Kpro device having deployable flexible haptics that is suitable for minimally invasive surgical techniques.
Figure 19B:
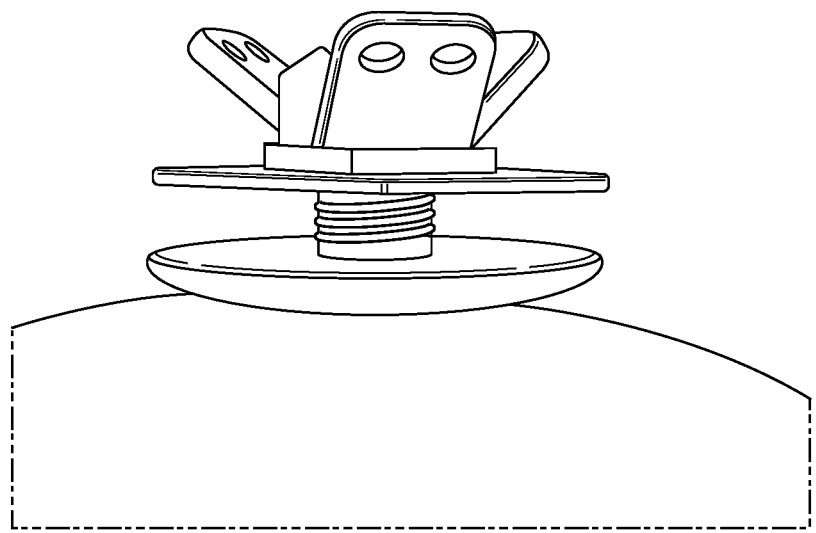
Figure 19C:
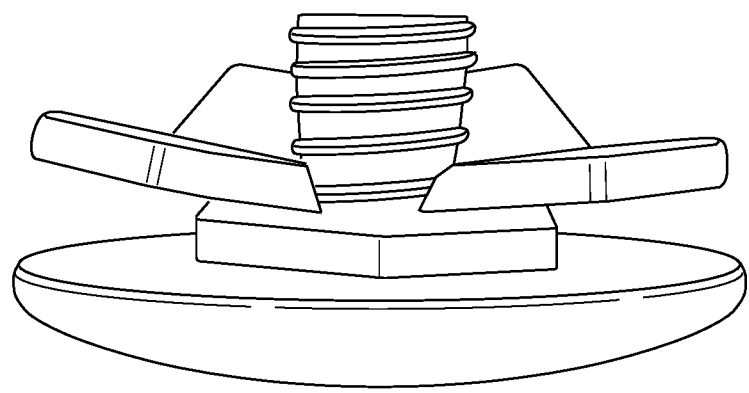

A minimally invasive Kpro device having a separable anchor body and front plate was designed. FIGS. 19A-19C show images of a two-part Kpro device having deployable flexible haptics that is suitable for minimally invasive surgical techniques. Flexible haptics were attached to the anchor body. FIG. 19A shows the two-part Kpro device with the anchor body coupled to the distal end of the threaded stem of the front plate. In FIG. 19A, the flexible haptics are in the closed configuration. FIG. 19B shows the two-part Kpro device where the anchor body that has been partially screwed onto the stem of the front plate. FIG. 19B shows the flexible haptics in a partially open position as they begin to expand outward from the center of the anchor body. FIG. 19C shows the two-part Kpro device where the anchor body has been completely screwed down onto the stem of the front plate such that the anchor body is in contact with the top portion of the front plate. FIG. 19C shows the flexible haptics in a fully open and expanded configuration.

Example 3

Figure 20:
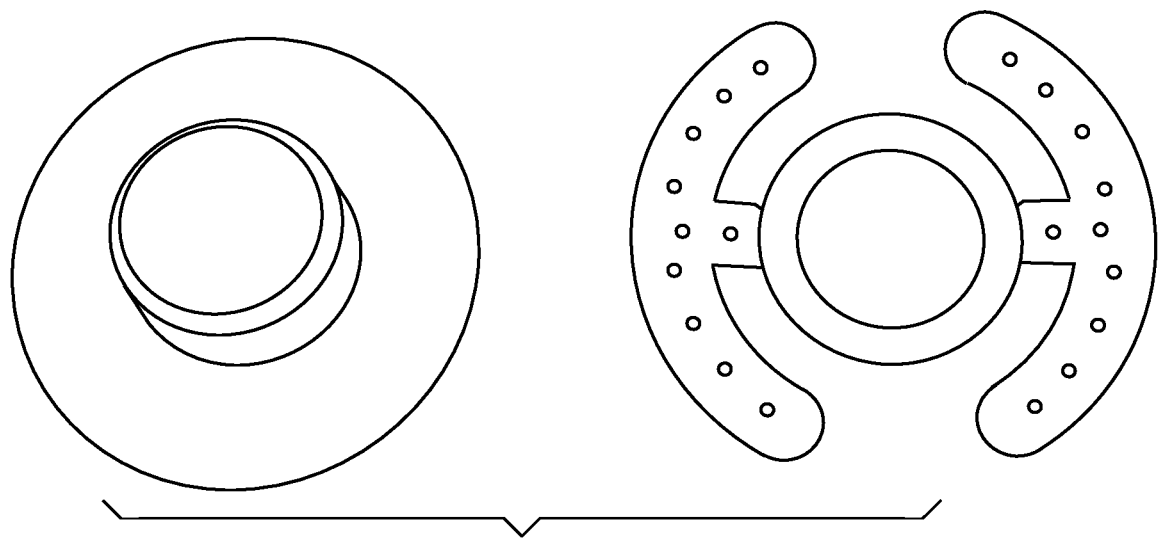
FIG. 20 shows an image of a two-part Kpro device having deployable flexible haptics where the front plate and the posterior anchor are not yet coupled.
Figure 21:
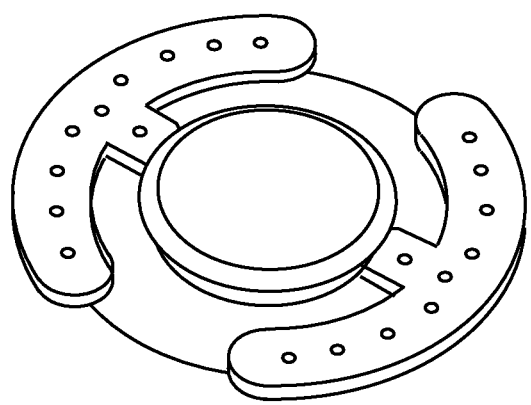
FIG. 21 shows an image of the two-part Kpro device of FIG. 18, where the front plate is coupled to the posterior anchor.

FIGS. 20 and 21 show images of another two-part Kpro device having a separable anchor body and front plate. In FIG. 20, the front plate (left) is shown separated from the anchor body having flexible haptics (right). The front plate is upside down with the stem portion facing up. FIG. 21 shows an image of the front plate and anchor body of FIG. 20 coupled together. The stem of the front plate can be inserted into the ring of the anchor body.

Example 4

Figure 22:
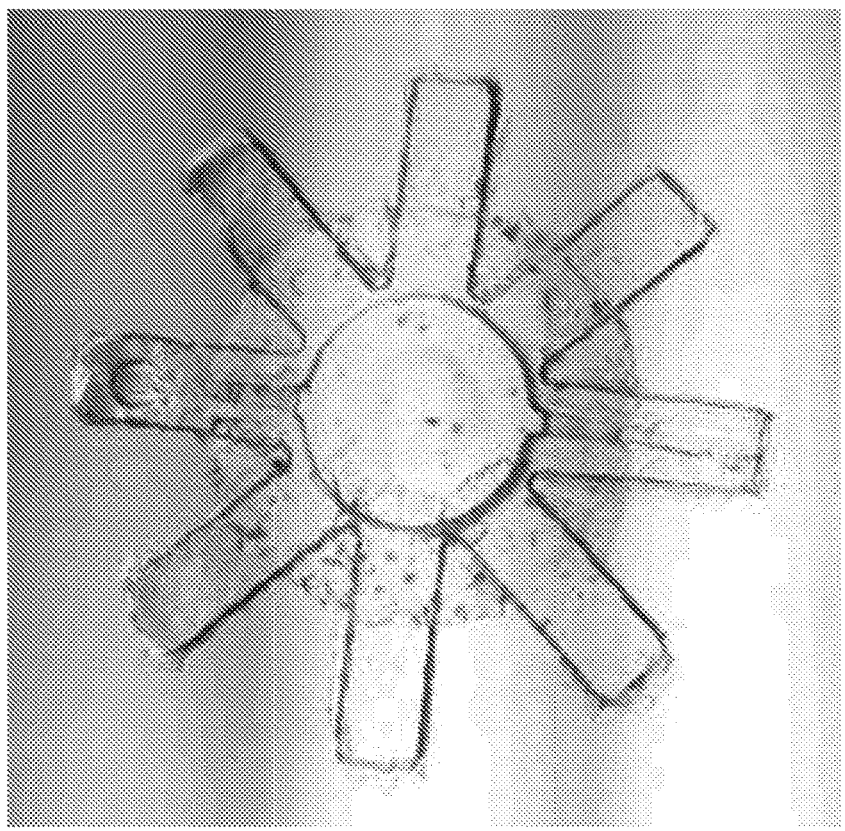
FIG. 22 shows a bright field microscopic image of a Kpro device composed of molded acrylic copolymer (phenylethylmethacrylate and phenyethyl acrylate).
Figure 23:
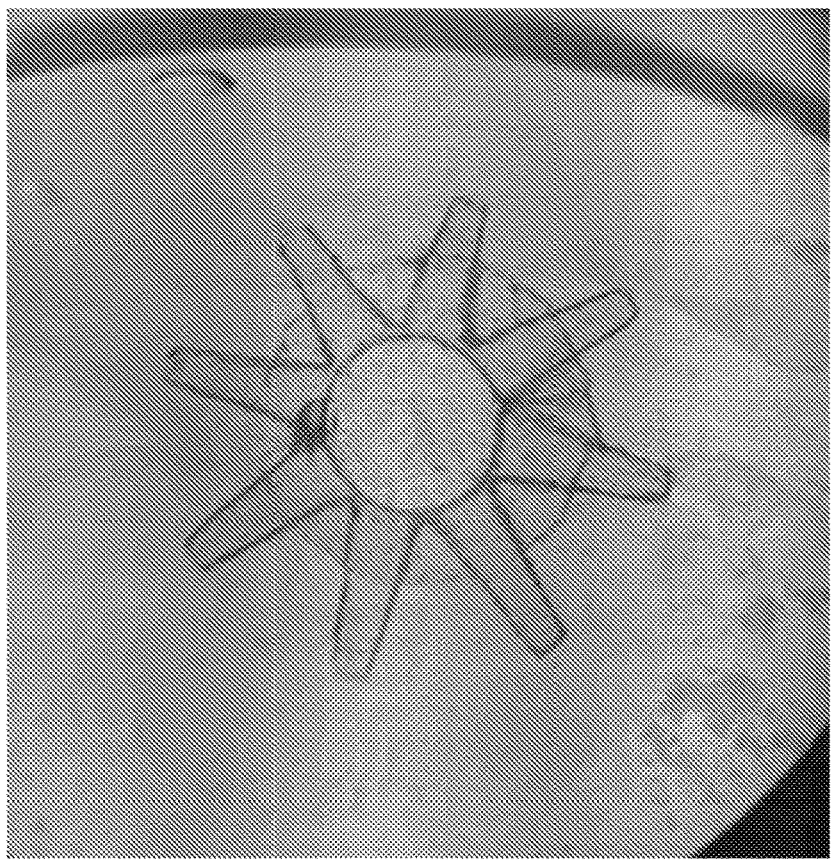
FIG. 23 shows a bright field microscopic image of a Kpro device composed of molded acrylic copolymer (phenylethylmethacrylate and phenyethyl acrylate).

A uni-body minimally invasive Kpro device having a anchor body with flexible haptics was made. FIGS. 22 and 23 show photographic images of uni-body minimally invasive Kpro devices. Briefly, a mixture of phenylethyl methacrylate and phenylethyl acrylate, hexanediol crosslinking agent and benzoyl peroxide activating agent is placed in a mold and heated for 4 hours at 90 C. Then the mold is allowed to cool and the formed kpro is carefully removed. The kpro is cleaned in 100% ethanol wash.

Example 5

The uni-body minimally invasive Kpro devices of Example 4 were implanted into rabbit eyes. Briefly, rabbits were placed under general anesthesia. The eye was sterilized with 5% iodine. A cataract surgery was performed. An incision about 3 mm in length was made in the central cornea suing a 3 mm biopsy punch. The keratoprosthesis was examined for defects. The flexible haptics (arms) were flexed together such that they were in the closed position with a circular tweezer tool. The flexible haptics were then inserted into the 3 mm surgical incision. The arms were then allowed to relax and expand into their open position in the anterior chamber of the eye to hold the keratoprosthesis in place. The rabbits were recovered, photographed, and OCT was performed at weekly intervals. At specific time points post-implantation (e.g. 1 and 3 months) the rabbits were euthanized and eye tissue was collected and examined for pathology.

Results at 4 Weeks Post-Implantation

Figure 24:
FIG. 24 shows a photographic image of a rabbit eye implanted with a Kpro device at 4 weeks post implantation.

FIG. 24 shows a photographic image of a rabbit eye implanted with a Kpro device at 4 weeks post implantation. Mild vascularization and scarring around the device was observed. However, a clear view into the eye was maintained.

Figure 25:
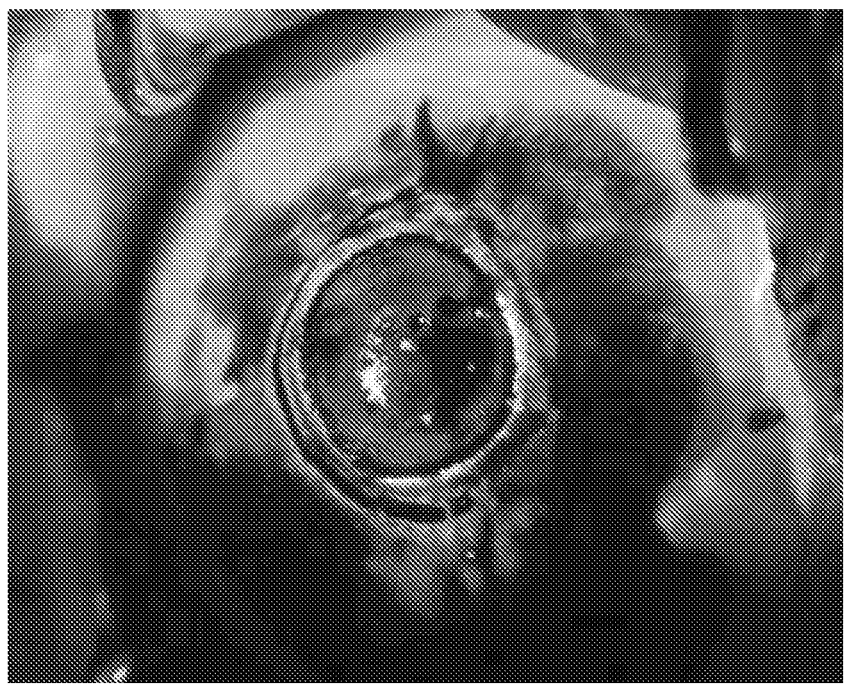
FIG. 25 shows a cobalt blue slit lamp photograph of eye stained with fluorescein dye of the eye implanted with a Kpro device of FIG. 24. This image can demonstrate intact corneal epithelium around implanted Kpro device.

FIG. 25 shows a cobalt blue photograph of the eye implanted with a Kpro device of FIG. 24. This demonstrates an intact corneal epithelium around the implanted Kpro device.

Figure 26:
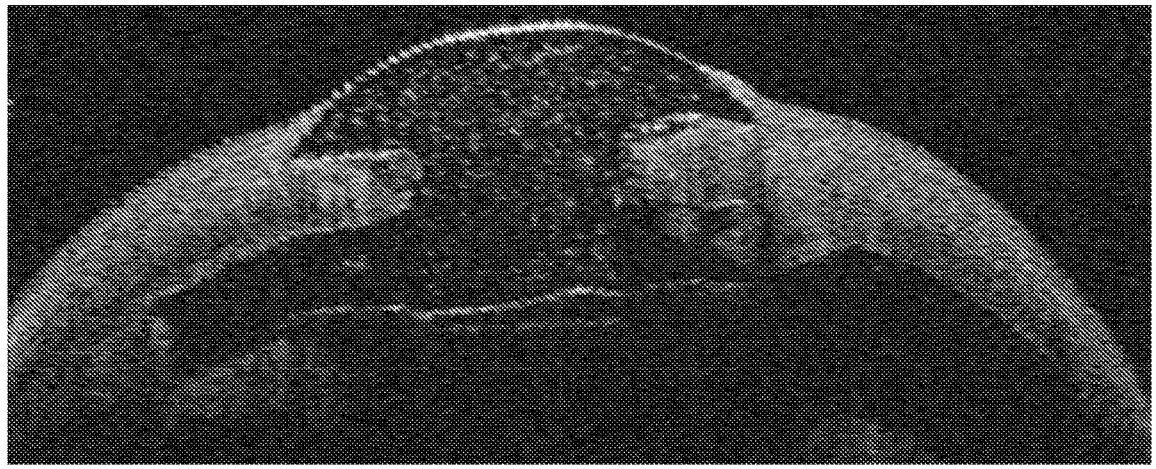
FIG. 26 shows an optical coherence tomography (OCT) image of the rabbit eye implanted with the Kpro device of FIG. 24.

FIG. 26 shows an optical coherence tomography (OCT) image of the rabbit eye implanted with the Kpro device of FIG. 24. This demonstrates that the Kpro device is well sandwiched around the cornea and that there is no significant breakdown of tissues in the areas in contact with the Kpro device.

Figure 27:
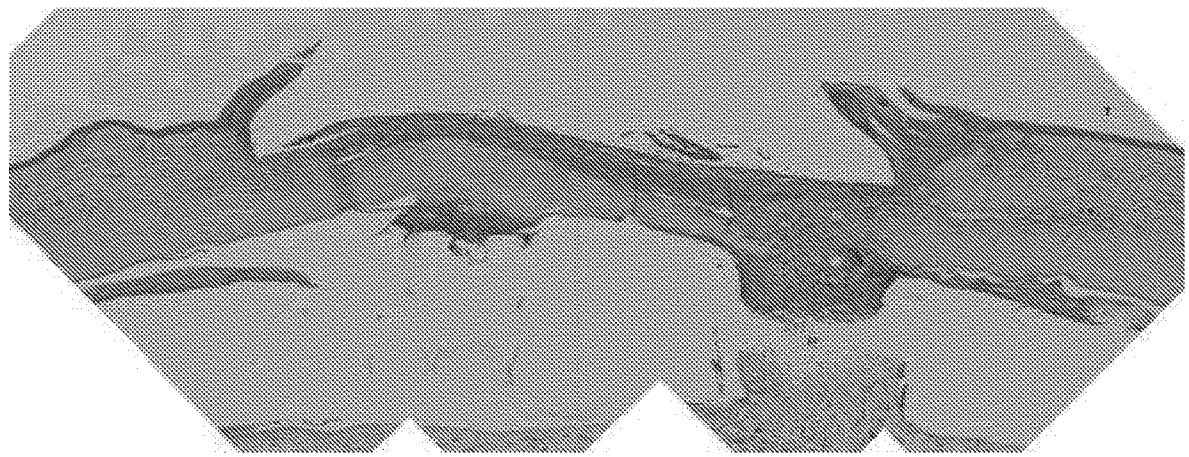
FIG. 27 shows a microscopic image of histology with hematoxylin and eosin (H and E) staining of the rabbit eye implanted with the Kpro device of FIG. 24.

FIG. 27 shows a microscopic image of histology of the rabbit eye implanted with the Kpro device of FIG. 24. Intact corneal epithelium was observed, which is able to grow onto where the Kpro device was. Only a mild inflammatory reaction was observed.

Results at 12 Weeks Post-Implantation

Figure 28:
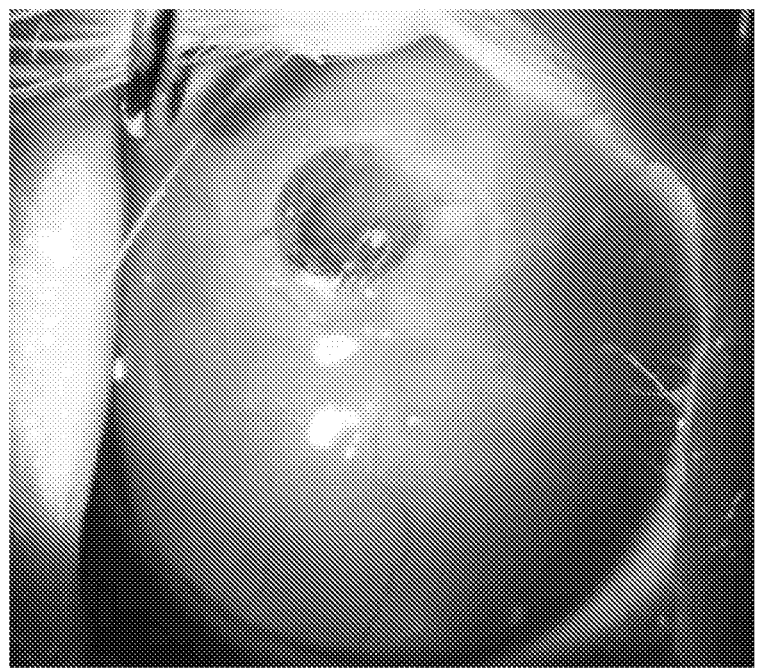
FIG. 28 shows a photographic image of a rabbit eye implanted with a Kpro device at 12 weeks post implantation.

FIG. 28 shows a photographic image of a rabbit eye implanted with a Kpro device at 12 weeks post implantation. The Kpro device maintains a pathway for light to enter the eye after 12 weeks of implantation. No scarring which blocks light from entering the eye was observed.

Figure 29:
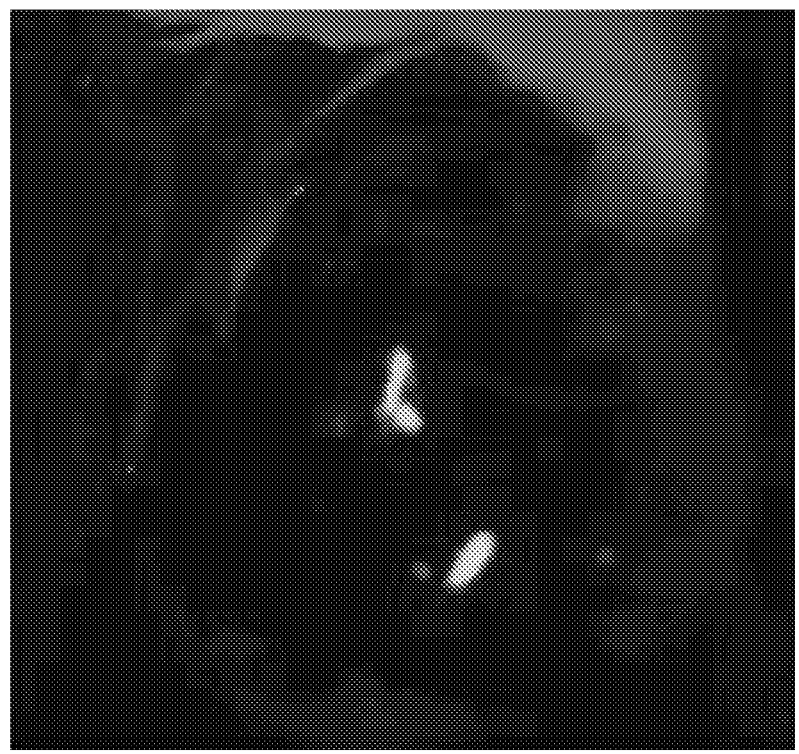
FIG. 29 shows a cobalt blue slit lamp photograph of eye stained with fluorescein dye of the eye implanted with a Kpro device of FIG. 28. This image can demonstrate no leakage of fluid around implanted kpro (seidel test).
Figure 30:
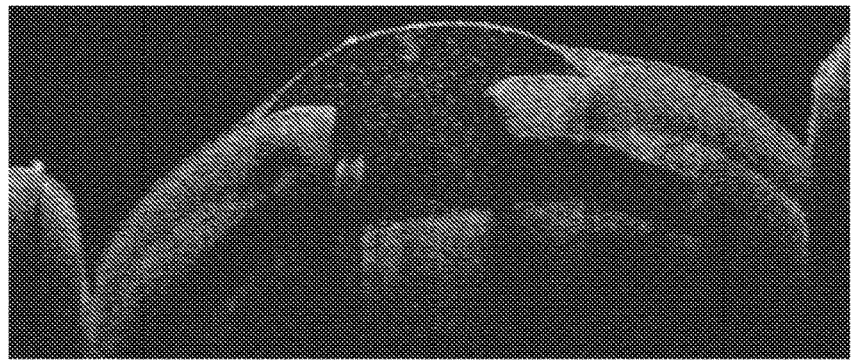
FIG. 30 shows an OCT image of the rabbit eye implanted with the Kpro device of FIG. 28. This can demonstrate intact cornea in the eye implanted with the Kpro device.

FIG. 29 shows a cobalt blue photograph of the eye implanted with a Kpro device of FIG. 28. Fluorescein stain and cobalt blue demonstrates that there was no leakage of fluid (seidel test) around the Kpro device at 3 months post-implantation FIG. 30 shows an OCT image of the rabbit eye implanted with the Kpro device of FIG. 28. This demonstrates that the Kpro device was well sandwiched around the cornea and that there was no significant breakdown of tissues in the areas in contact with the Kpro device.

Figure 31:
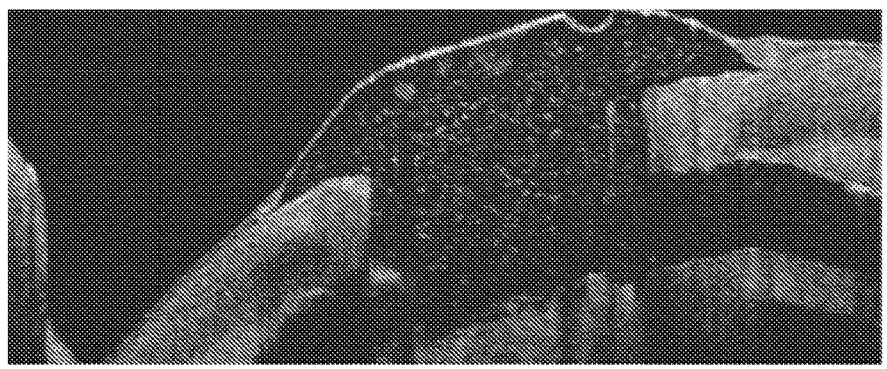
FIG. 31 shows an OCT image of the rabbit eye implanted with the Kpro device of FIG. 28.

FIG. 31 shows an OCT image of the rabbit eye implanted with the Kpro device of FIG. 28. FIG. 31 is a higher resolution scan of a slightly different cross section of the same eye as 30. This can demonstrate intact cornea in the eye implanted with the Kpro device.

Figure 32:
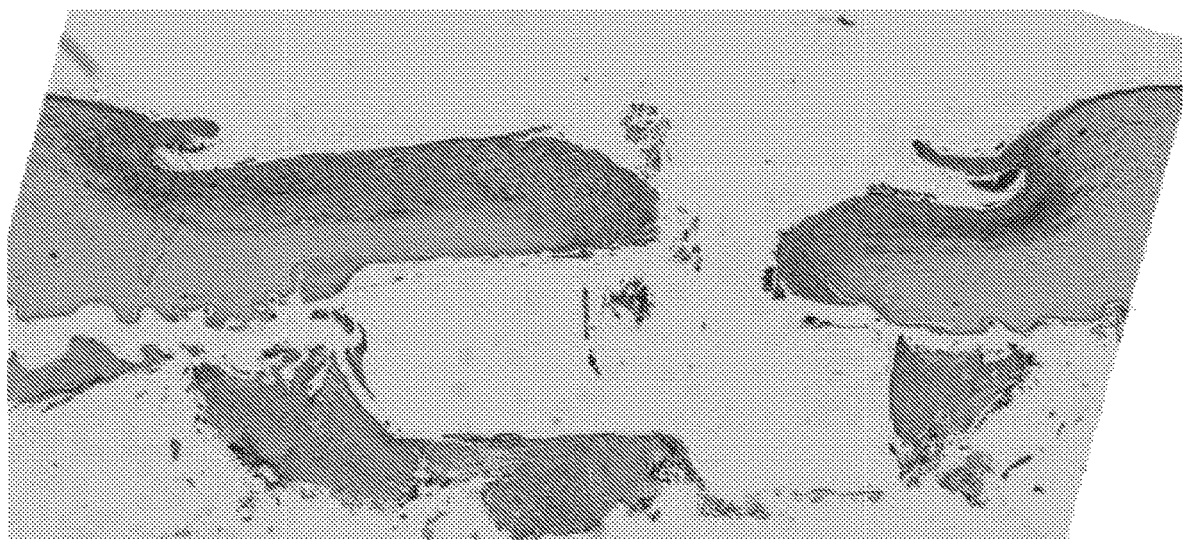
FIG. 32 shows a microscopic image of histology with hematoxylin and eosin (H and E) staining of the rabbit eye implanted with the Kpro device of FIG. 28.

FIG. 32 shows a microscopic image of histology with hematoxylin and eosin (H and E) staining of the rabbit eye implanted with the Kpro device of FIG. 28. H and E stain histology can demonstrate that there is intact corneal epithelium which is able to grow onto where the kpro was. Only a moderate inflammatory reaction was observed.

We claim:
1. A keratoprosthesis (Kpro) device comprising:
an anchor body; and
a plurality of flexible haptics, wherein the plurality of flexible haptics are attached to and are capable of extending radially from the anchor body, the anchor body is configured to couple to a front plate during implantation, the front plate comprises an anterior portion and a posterior stem portion, the stem portion is configured to couple to the anchor body during implantation, the stem portion is threaded, and the anchor body is configured to be screwed onto the stem during implantation.

2. The Kpro device of claim 1, further comprising a front plate, wherein the front plate is attached to the anchor body such that the Kpro device is a single implantable device.

3. The Kpro device of claim 2, wherein the anchor body is a cannula or a cylinder.

4. The Kpro device of claim 2, wherein the anchor body has an inner diameter and an outer diameter, wherein the inner diameter ranges from about 1 mm to about 8 mm, and wherein the outer diameter ranges from about 1 mm to about 8 mm.

5. The Kpro device of claim 4, wherein a diameter of the front plate is the same as the outer diameter of the anchor body.

6. The Kpro device of claim 4, wherein a diameter front plate is of the different than the outer diameter of the anchor body.

7. The Kpro device of claim 6, wherein the diameter of the front plate is larger than the outer diameter of the anchor body.

8. The Kpro device of claim 2, wherein the anchor body has a height of about 0.5 mm to about 3 mm as measured from the bottom of the anchor body to the bottom of the front plate.

9. The Kpro device of claim 2, wherein the front plate is curved along the portion of the front plate that is distal to the anchor body.

10. The Kpro device of claim 2, wherein the front plate forms a half-sphere.

11. The Kpro device of claim 2, wherein the plurality of haptics are all attached to the anchor body at the same height along the circumference of the anchor body as measured from the bottom of the anchor body.

12. The Kpro device of claim 2, wherein all components of the Kpro device are flexible.

13. The Kpro device of claim 2, wherein the Kpro device is implantable using a minimally invasive incision.

14. The Kpro device of claim 13, wherein the minimally invasive incision is about 3 mm.

15. The Kpro device of claim 1, wherein the anchor body is a ring having an inner diameter and an outer diameter ranges from about 1 mm to about 8 mm, and wherein the inner diameter ranges from about 1 mm to about 8 mm.

16. The Kpro device of claim 1, wherein the anterior portion of the front plate is substantially round as measured along a first axis.

17. The Kpro device of claim 1, wherein the stem portion is a cannula or a solid cylinder, and wherein the stem portion has an outer diameter.

18. The Kpro device of claim 17, wherein the diameter of the anterior portion of the front plate as measured along the first axis is the same as the outer diameter of the stem portion as measured along the same axis.

19. The Kpro device of claim 18, wherein the diameter of the anterior portion of the front plate as measured along the first axis is different than the outer diameter of the stem portion as measured along the same axis.

20. The Kpro device of claim 1, wherein at least one of the plurality of haptics can have a hole.

21. The Kpro device of claim 1, wherein the plurality of haptics are in a first position prior to implantation and a second position after implantation, wherein the plurality of haptics are folded in towards the anchor body when in the first position and are extended radially away from the anchor body when in the second position.

\* \* \* \* \*